(12) United States Patent
Defrees

(10) Patent No.: US 10,555,959 B2
(45) Date of Patent: Feb. 11, 2020

(54) GLYCOLIPIDS AS TREATMENT FOR DISEASE

(71) Applicant: La Jolla Pharmaceutical Company, San Diego, CA (US)

(72) Inventor: Shawn Defrees, North Wales, PA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 176 days.

(21) Appl. No.: 14/949,812

(22) Filed: Nov. 23, 2015

(65) Prior Publication Data

US 2016/0151401 A1 Jun. 2, 2016

Related U.S. Application Data

(63) Continuation of application No. 13/260,553, filed as application No. PCT/US2010/028725 on Mar. 25, 2010, now abandoned.

(60) Provisional application No. 61/293,200, filed on Jan. 7, 2010, provisional application No. 61/244,735, filed on Sep. 22, 2009, provisional application No. 61/220,151, filed on Jun. 24, 2009, provisional application No. 61/180,346, filed on May 21, 2009, provisional application No. 61/180,098, filed on May 20, 2009, provisional application No. 61/163,371, filed on Mar. 25, 2009.

(51) Int. Cl.
*A61K 31/7028* (2006.01)
*A61K 31/715* (2006.01)
*A61K 31/7032* (2006.01)
*A61K 31/70* (2006.01)

(52) U.S. Cl.
CPC ...... *A61K 31/7028* (2013.01); *A61K 31/7032* (2013.01); *A61K 31/715* (2013.01)

(58) Field of Classification Search
None
See application file for complete search history.

(56) References Cited

U.S. PATENT DOCUMENTS

| | | |
|---|---|---|
| 3,954,881 A | 5/1976 | Bowler |
| 4,252,951 A | 2/1981 | Jackson et al. |
| 4,347,244 A | 8/1982 | Mynard et al. |
| 4,476,119 A | 10/1984 | Della Valle et al. |
| 4,593,091 A | 6/1986 | Della Valle et al. |
| 4,639,437 A | 1/1987 | Della Valle et al. |
| 4,707,469 A | 11/1987 | Della Valle et al. |
| 4,710,490 A | 12/1987 | Catsimpoolas et al. |
| 4,713,374 A | 12/1987 | Della Valle et al. |
| 4,716,223 A | 12/1987 | Della Valle et al. |
| 4,849,413 A | 7/1989 | Della Valle et al. |
| 4,940,694 A | 7/1990 | Della Valle et al. |
| 5,045,532 A | 9/1991 | Della Valle et al. |
| 5,135,921 A | 8/1992 | Della Valle et al. |
| 5,183,807 A | 2/1993 | Della Valle et al. |
| 5,190,925 A | 3/1993 | Della Valle et al. |
| 5,210,185 A | 5/1993 | Della Valle et al. |
| 5,218,094 A | 6/1993 | Della Valle |
| 5,229,373 A | 7/1993 | Della Valle |
| 5,260,464 A | 11/1993 | Della Valle et al. |
| 5,264,424 A | 11/1993 | Della Valle et al. |
| 5,350,841 A | 9/1994 | Romeo et al. |
| 5,409,817 A | 4/1995 | Ito et al. |
| 5,424,294 A | 6/1995 | Della Valle et al. |
| 5,484,775 A | 1/1996 | Della Valle et al. |
| 5,519,007 A | 5/1996 | Della Valle et al. |
| 5,521,164 A | 5/1996 | Della Valle et al. |
| 5,523,294 A | 6/1996 | Della Valle et al. |
| 5,677,285 A | 10/1997 | Romeo et al. |
| 5,792,858 A | 8/1998 | Della Valle et al. |
| 5,795,869 A | 8/1998 | Romeo et al. |
| 5,849,717 A | 12/1998 | Romeo et al. |
| 5,922,577 A | 7/1999 | DeFrees et al. |
| 6,030,815 A | 2/2000 | DeFrees et al. |
| 6,060,526 A | 5/2000 | Tasaki |
| 6,284,493 B1 | 9/2001 | Roth |
| 6,331,418 B1 | 12/2001 | Roth |
| 6,413,935 B1 | 7/2002 | Sette et al. |
| 6,440,703 B1 | 8/2002 | DeFrees |
| 7,273,852 B2 | 9/2007 | Tsuji et al. |
| 7,842,677 B2 | 11/2010 | DeFrees et al. |
| 7,888,331 B2 | 2/2011 | DeFrees et al. |
| 7,932,236 B2 | 4/2011 | DeFrees et al. |
| 2001/0004683 A1 | 6/2001 | Gambale et al. |
| 2002/0072502 A1 | 6/2002 | Ho |

(Continued)

FOREIGN PATENT DOCUMENTS

DE 19709787 A1 9/1998
DE 19733255 A1 2/1999

(Continued)

OTHER PUBLICATIONS

Schneider, Ann N Y Acad Sci. Jun. 19, 1998;845:363-73.*
Buschard, K. et al., "Treatment with Sulfatide or its Precursor, Galactosylceramide, Prevents Diabetes in NDD Mice", Autoimmunity, Informa Healthcare, GB, vol. 34, No. 1, pp. 9-17, 2001.
Desplats P.A. et al."Glycolipid and Ganglioside Metabolism Imbalances in Huntington's Disease", Neurolobiology of Disease v. 27 n. 3 p. 265-277.
Dube et al. "Glycans in Cancer and Inflammation Potential for Therapeutics and Diagnostics", Nature Review Drug Discovery, vol. 4; pp. 477-488, 2005.
Institute for International Medical Education, definition of "prevention", [online] Retrieved from the internet http://www.iime.org/glossary.htm , pp. 1,2,26, 27 and 39, Published Feb. 2002.

(Continued)

*Primary Examiner* — Layla D Berry
(74) *Attorney, Agent, or Firm* — Foley Hoag LLP; David P. Halstead; Lucas P. Watkins

(57) ABSTRACT

This invention provides compounds, compositions, and methods for treating a disorder selected from cancer, hyperinsulinemia, hypoglycemia, hyperinsulinemia with hypoglycemia, atypical Parkinson's disease, Huntington's disease, multiple systems atrophy, GM3 synthase deficiency, GM2 synthase deficiency or tauopathy.

10 Claims, 7 Drawing Sheets

(56) References Cited

U.S. PATENT DOCUMENTS

| | | | |
|---|---|---|---|
| 2004/0063911 A1 | 4/2004 | DeFrees et al. |
| 2005/0032742 A1 | 2/2005 | DeFrees et al. |
| 2005/0239741 A1 | 10/2005 | Defrees et al. |
| 2005/0245735 A1 | 11/2005 | DeFrees et al. |
| 2007/0275908 A1 | 11/2007 | Defrees et al. |
| 2008/0125392 A1 | 5/2008 | DeFrees et al. |
| 2009/0170155 A1 | 7/2009 | Johnson et al. |

FOREIGN PATENT DOCUMENTS

| | | | |
|---|---|---|---|
| EP | 0119539 A2 | 9/1984 |
| EP | 0410881 A2 | 7/1990 |
| EP | 557580 A1 | 9/1993 |
| EP | 577580 A2 | 1/1994 |
| EP | 1911850 A1 | 4/2008 |
| JP | 09208461 | 8/1997 |
| WO | WO 92/16640 A1 | 10/1992 |
| WO | WO 93/03049 A1 | 2/1993 |
| WO | WO-93/18787 A1 | 9/1993 |
| WO | WO 98/15581 A1 | 4/1998 |
| WO | WO-98/40390 A2 | 9/1998 |
| WO | WO 98/52577 A1 | 11/1998 |
| WO | WO-99/28491 A1 | 6/1999 |
| WO | WO-00/046379 A1 | 8/2000 |
| WO | WO 01/04341 A1 | 1/2001 |
| WO | WO-0100434 A1 | 1/2001 |
| WO | WO-03/011879 A1 | 2/2003 |
| WO | WO 03/016469 A2 | 2/2003 |
| WO | WO 03/017949 A2 | 2/2003 |
| WO | WO 03/031464 A2 | 4/2003 |
| WO | WO 04/080960 A2 | 9/2004 |
| WO | WO 05/118798 A2 | 12/2005 |

OTHER PUBLICATIONS

Medical News Today, "*What is Huntington's Disease? What causes Huntington's Disease?*", Retrieved May 11, 2015. Retrieved from the internet at http://www.medicalnewstoday.com/articles/159552.php (2014).
Defrees Shawn, "*Methods and Compositions for the Enzymatic Synthesis of Gangliosides*" U.S. Appl. No. 60/452,796, filed Mar. 6, 2003.
Defrees Shawn, "*Glycolipids*", U.S. Appl. No. 60/626,678, filed Nov. 9, 2004.
Fox, Todd, E., et al., "*Therapeutic Strategies for Diabetes and Complications: a Role for Sphingolipids?*", Advances in Experimental Med. and Biol., vol. 688, p. 206-216, 2010.
Maglione, V., et al., "*Impaired Ganglioside Metabolism in Huntington's Disease and Neuroprotective Role of GM1*", The J. of Neuroscience, vol. 30, No. 11, p. 4072-4080, Mar. 17, 2010.
Abdad-Rodriguez et al., "Regulation of axonal development by plasma membrane gangliosides", J Neurochem, 103(1):47-55 (2007).
Abe et al., "Improved inhibitors of glucosylceramide synthase", J Biochem, 111(2):191-196 (1992).
Anne et al., "Phosphorylation of huntingtin by cyclin-dependent kinase 5 is induced by DNA damage and regulates wild-type and mutant huntingtin toxicity in neurons", J Neurosci, 27(27):7318-7328 (2007).
Bae et al., "p53 Mediates Cellular Dysfunction and Behavioral Abnormalities in Huntington's Disease", Neuron, 47(1):29-41 (2005).
Chiavegatto et al., "A functional role for complex gangliosides: motor deficits in GM2/GD2 synthase knockout mice", Exp Neurol, 166(2):227-234 (2000).
Chinnock et al., "Gangliosides for acute spinal cord injury", Chochrane Database Syst Rev, 2(2):CD004444 (2005).
Ciarmiello et al., "Brain White-Matter Volume Loss and Glucose Hypometabolism Precede the Clinical Symptoms of Huntington's Disease", J Nucl Med, 47(2):215-222 (2006).
Da Silva et al., "Asymmetric membrane ganglioside sialidase activity specifies axonal fate", Nat Neurosci, 8:606-615 (2005).
Deplates et al., "Glycolipid and Ganglioside Metabolism Imbalances in Huntington's Disease," Neurobiol Dis, 27(3):265-277 (2007).
Dube et al. "Glycans in cancer and inflammation—potential for therapeutics and diagnostics," Nat Rev Drug Discov, 4:477-488 (2005).
Duchemin et al., "GM1-induced activation of phosphatidylinositol 3-kinase: involvement of Trk receptors", J Neurochem, 104(6):1466-1477 (2008).
Dunah et al., "Sp1 and TAFII130 transcriptional activity disrupted in early Huntington's disease", Science, 296(5576):2238-2243 (2002).
Favaron et al., "Gangliosides prevent glutamate and kainate neurotoxicity in primary neuronal cultures of neonatal rat cerebellum and cortex", PNAS, 85(19):7351-7355 (1988).
Ferrari et al., "Prevention of apoptotic neuronal death by GM1 ganglioside. Involvement of Trk neurotrophin receptors", J Biol Chem, 270(7):3074-3080 (1995).
Gauthier et al., "Huntingtin controls neurotrophic support and survival of neurons by enhancing BDNF vesicular transport along microtubules", Cell, 118(1):127-138 (2004).
Graham et al., "Cleavage at the caspase-6 site is required for neuronal dysfunction and degeneration due to mutant huntingtin", Cell, 125(6):1179-1191 (2006).
Hakomori, "Inaugural Article: The glycosynapse", PNAS, 99(5):225-232 (2002).
Harris et al., "The p53 pathway: positive and negative feedback loops", Oncogene, 24:2899-2908 (2005).
Holmgren et al., "Interaction of cholera toxin and membrane GM1 ganglioside of small intestine", PNAS, 72(7):2520-2524 (1975).
Humbert et al., "The IGF-1/Akt pathway is neuroprotective in Huntington's disease and involves Huntingtin phosphorylation by Akt", Dev Cell, 2(6):831-837 (2002).
Ichikawa et al., "Binding of laminin-1 to monosialoganglioside GM1 in lipid rafts is crucial for neurite outgrowth", J Cell Sci, (2009), vol. 122, pp. 289-299.
Imarisio et al., "Huntington's disease: from pathology and genetics to potential therapies", Biochem J, 412(2):191-209 (2008).
Kaplan et al., "Neurotrophin signal transduction in the nervous system", Curr Opin Neurobiol, 10(3):381-391 (2000).
Karten et al., "Generation and function of astroglial lipoproteins from Niemann-Pick type C1-deficient mice", Biochem J, 387(3):779-788 (2005).
Ladisch et al., "A solvent partition method for microscale ganglioside purification", Anal Biochem, 146(1):220-231 (1985).
Ledeen et al., "Thematic Review Series: Sphingolipids. Nuclear sphingolipids: metabolism and signaling", J Lipid Res, 49:1176-1186 (2008).
Lievens et al., "Expanded polyglutamine peptides disrupt EGF receptor signaling and glutamate transporter expression in Drosophila", Hum Mol Genet, 14(5):713-724 (2005).
Liu et al., "A genetic model of substrate deprivation therapy for a glycosphingolipid storage disorder", J Clin Invest, 103(4):497-505 (1999).
Lopez et al.,"Gangliosides in cell recognition and membrane protein regulation", Curr Opin Struct Biol., 19(5):549-557 (2009).
Luo et al., "Cdk5 phosphorylation of huntingtin reduces its cleavage by caspases: implications for mutant huntingtin toxicity", J Cell Biol, 169(4):647-656 (2005).
MacDonald et al., "A novel gene containing a trinucleotide repeat that is expanded and unstable on Huntington's disease chromosomes", Cell, 72(6):971-983 (1993).
Mangiarini et al., "Exon 1 of the HD gene with an expanded CAG repeat is sufficient to cause a progressive neurological phenotype in transgenic mice", Cell, 87(3):493-506 (1996).
Oppenheimer, "GM1 ganglioside therapy in acute ischemic stroke", Stroke, 21:825 (1990).
Prinetti et al.,"Glycosphingolipid behaviour in complex membranes", Biochim Biophys Acta, 1788(1):184-193 (2009).
Rabin et al., "Gangliosides activate Trk receptors by inducing the release of neurotrophins", J Biol Chem, 277(51):29466-49472 (2002).
Rigamont et al., "Huntingtin's neuroprotective activity occurs via inhibition of procaspase-9 processing", J Biol Chem, (2001), vol. 276, pp. 14545-14548.

(56) References Cited

OTHER PUBLICATIONS

Schilling et al., "Huntingtin phosphorylation sites mapped by mass spectrometry. Modulation of cleavage and toxicity", J Biol Chem, 281(33):23686-23697 (2006).
Abad-Rodriguez et al., "Purification and Structure of Neurostatin, an Inhibitor of Astrocyte Division of Mammalian Brain," JNC, 74(6):2547-2556 (2000).
Akerud et al., "Neuroprotection through delivery of glial cell line-derived neurotrophic factor by neural stem cells in a mouse model of Parkinson's disease," J Neurosci. 21: 8108-8118 (2001).
Alais et al., "Syntheses of linear tetra-, hexa-, and octa-saccharide fragments of the i-blood group active poly-(N-acetyl-lactosamine) series. Blockwise methods for the synthesis of repetitive oligosaccharide sequences," Carbohydrate Res, 207(1):11-31 (1990).
Allen et al., "Pursuit of Optimal Carbohydrate-Based Anticancer Vaccines:? Preparation of a Multiantigenic Unimolecular Glycopeptide Containing the Tn, MBr1, and Lewisy Antigens," J Am Chem Soc, 123(9):1890-1897 (2001).
Alter, "GM1 ganglioside for acute ischemic stroke", Ann NY Acad Sci, 845(1):391-401 (1998).
Anumula et al., "High resolution and high sensitivity methods for oligosaccharide mapping and characterization by normal phase high performance liquid chromatography following derivatization with highly fluorescent anthranilic acid," Glycobiol, 8(7):685-694 (1998).
Beith-Halahmi et al., "Synthesis of O-β-d-galactopyranosyl-(1→3)-O-β-d-galactopyranosyl-(1→4)-d-glucose," Carbohydrate Res, 5:25-30 (1967).
Bertozzi et al., "Carbon-linked galactosphingolipid analogs bind specifically to HIV-1 gp120," J Am Chem Soc, 114(26):10639-10641 (1992).
Binder et al., "Galactosylation by use of β-galactosidase: Chemoenzymatic syntheses of di-and trisaccharides," Tetrahedron, 50(35):10407-10418 (1994).
Braak et al., "Staging of brain pathology related to sporadic Parkinson's disease," Neurobiol. Aging. 24: 197-211 (2003).
Braga et al., "Making crystals from crystals: a green route to crystal engineering and polymorphism," Chem Comm, 29:3635-3645 (2005).
Bruun et al., "Sulfatide increases adiponectin and decreases TNF-α, IL-6, and IL-8 in human adipose tissue in vitro," Mol Cell Endocrinol, 263(1-2):142-148 (2007).
Buschard et al., "C16:0 Sulfatide Inhibits Insulin Secretion in Rat β-Cells by Reducing the Sensitivity of KATP Channels to ATP Inhibition," Diabetes, 55:2826-2834 (2006).
Cattaneo et al., "Generation and characterization of embryonic striatal conditionally immortalized ST14A cells", J Neurosci Res, 53(2):223-234 (1998).
Chao et al., "Integrin av and NCAM mediate the effects of GDNF on DA neuronsurvival, outgrowth, DA turnover and motor activity in rats," Neurobiol. Aging. 24: 105-116 (2003).
Chen, Handbook of Carbohydrate Engineering, CRC Press, (2005), pp. 1-48.
Chester et al., "IUPAC-IUB Joint Commission on Biochemical Nomenclature (JCBN) Nomenclature of glycolipids Recommendations 1997," Eur J Biochem, 257:293-298 (1998).
Chester, "Nomenclature of Glycolipids (IUPAC Recommendations 1997)," Pure Appl Chem, 69(12):2475-2487 (1997).
Choi-Lundberg et al., "Dopaminergic neurons protected from degeneration by GDNF gene therapy," Science 275: 838-841 (1997).
Ciesielska et al., "Anterograde axonal transport of AAV2-GDNF in rat basal ganglia," Mol. Ther. 19: 922-927 (2011).
Clarke et al., "A one-hit model of cell death in inherited neuronal degenerations", Nature, 406:195-199 (2000).
Colin et al., "Akt is altered in an animal model of Huntington's disease and in patients", Eur J Neurosci, 21(6):1478-1488 (2005).
Collier et al., "Ageing as a primary risk factor for Parkinson's disease: evidence from studies of non-human primates," Nat. Rev. Neurosci. 12: 359-366 (2011).
Crowder et al., "Dok-6, a Novel p62 Dok family member, promotes Ret-mediated neurite outgrowth," J Biol. Chem. 279: 42072-42081 (2004).
De Rosa et al., "Aliphatic and Aromatic Glycosides from the Cell Cultures of Lycopersicon Esculentum," Phytochem, 42(4):1031-1034 (1996).
Decker et al., "Immunostimulatory CpG-oligonucleotides cause proliferation, cytokine production, and an immunogenic phenotype in chronic lymphocytic leukemia B cells," Blood, 95:999-1006 (2000).
Doherty et al., "Ganglioside GM1 does not initiate, but enhances neurite regeneration of nerve growth factor-dependent sensory neurons," J. Neurochem. 44: 1259-1265 (1985).
Dreyfus et al., "Successive Isolation and Separation of the Major Lipid Fractions Including Gangliosides from Single Biological Samples," Anal Biochem, 249:67-78 (1997).
Eberling et al., "Functional effects of AAV2-GDNF on the dopaminergic nigrostriatal pathway in parkinsonian rhesus monkeys," Hum. Gene Ther. 20: 511-518 (2009).
Eslamboli et al., "Continuous low-level glial cell line-derived neurotrophic factor delivery using recombinant adena-associated viral vectors provides neuroprotection and induces behavioral recovery in a primate model of Parkinson's disease," J Neurosci. 25: 769-777 (2005).
Fan et al., "N-methyl-D-aspartate (NMDA) receptor function and excitotoxicity in Huntington's disease", Prog Neurobiol, 81(5-6):272-293 (2007).
Ferrari et al., "Gangliosides Enhance Neurite Outgrowth in PC12 Cells," Dev. Brain Res. 8: 215-221 (1983).
Fishman et al., "Deficient Ganglioside Biosynthesis: a novel human sphingolipidosis", Science, 187(4171):68-70 (1975).
Frost et al., "Effect of phenylarsine oxide on insulin-dependent protein phosphorylation and glucose transport in 3T3-L1 adipocytes," J Biol Chem, 262:9872-9876 (1987).
Fujimoto et al., "Ganglioside GM3 inhibits proliferation and invasion of glioma," J Neuro-Oncology, 71:99-106 (2005).
Furuse et al., "Effect of the mono- and tetra-sialogangliosides, GM1 and GQ1 b, on long-term potentiation in the CA1 hippocampal neurons of the guinea pig", Exp Brain Res, 123(3):307-314 (1998).
Gash et al., "Gerhardt, Functional recovery in parkinsonian monkeys treated with GDNF," Nature 380: 252-255 (1996).
Gill "Direct brain infusion of glial cell line-derived neurotrophic factor in Parkinson disease," Nat. Med. 9: 589-595 (2003).
Gilman, "Parkinsonian Syndromes," Clin Geriatric Med, 22:827-842 (2006).
Gimenez et al., "Image-guided convection-enhanced delivery of GDNF protein into monkey putamen," Neuroimage. 54: S189-S195 (2011).
Grudler et al., "Anwendung des trichloracetimidatverfahrens auf 2-desoxy-2-phthalimido-d-glucose-derivative. Synthese von oligosachariden der "Core-Region" von O-glycoproteinen des mucintyps," Carbohydrate Res, 135(2):203-218 (1985).
Guadino et al., "A Novel and Efficient Synthesis of Neolacto Series Gangliosides 3'-nLM1 and 6'-nLM1," J Am Chem Soc, 116:1149-1150 (1994).
Guivisdalsky et al., "Synthesis and Antineoplastic Properties of Ether-Linked Thioglycolipids," J Med Chem, 33(9):2614-2621 (1990).
Hadjiconstantinou et al., "Administration of GM1 ganglioside restores the dopamine content in striatum after chronic treatment with MPTP," Neuropharmacology 25: 1075-1077 (1986).
Hadjiconstantinou et al., "GM1 ganglioside-induced recovery of nigrostriatal dopaminergic neurons after MPTP: an immunohistochemical study," Brain Res. 484: 297-303 (1989).
Harjes et al., "The hunt for huntingtin function: interaction partners tell many different stories", Trends Biochem Sci, 28(8):425-433 (2003).
Hasegawa et al., "Synthetic Studies on Sialoglycoconjugates 23: Total Synthesis of Sialyl-α(2□6)-Lactotetraosylceramide and Sialyl-α(2□6)-Neolactotetraosylceramide," J Carbohydrate Chem, 10(3):439-459 (1991).
Helling et al., "GD3 Vaccines for Melanoma: Superior Immunogenicity of Keyhole Limpet Hemocyanin Conjugate Vaccines," Cancer Res, 54:197-203 (1994).
Hickey et al., "Apoptosis in Huntington's disease", Prog Neuropsychopharmacol Biol Psychiatry, 27(2):255-265 (2003).

(56) References Cited

OTHER PUBLICATIONS

Hong et al., "Highly Active Water-Soluble Olefin Metathesis Catalyst," J Am Chem Soc, 128(11):3508-3509 (2006).
Horowitz, "Ganglioside (Cronassial) therapy in diabetic neuropathy," Adv. Exp. Med. And Biol. 174: 593-600 (1984).
Ito et al., "A Novel Strategy for Synthesisi of Ganglioside GM# Using an Enzymatically Produced Sialoside Glycosi Donor," J Am Chem Soc, 115(4):1603-1605 (1993).
Jennemann et al., "Specific Immunization Using Keyhole Limpet Hemocyanin-Ganglioside Conjugates," J Biochem, 115(6):1047-1052 (1994).
Johnston et al., "Clinically relevant effects of convection-enhanced delivery of AA V2-GDNF on the dopaminergic nigrostriatal pathway in aged rhesus monkeys," Hum. Gene Ther. 20: 497-510 (2009).
Kameyama et al., "Total synthesis of sialyl lactotetraosyl ceramide," Carbohydrate Res, 193:C1-C5 (1989).
Kanamori et al., "Deaminated neuraminic acid-rich glycoprotein of rainbow trout egg vitelline envelope. Occurrence of a novel alpha-2,8-linked oligo(deaminated neuraminic acid) structure in O-linked glycan chains," J Biol Chem, 265:21811-21819 (1990).
Kanda et al., "Gangliosides GD1b, GT1b, and GQ1b Suppress the Growth of Human Melanoma by Inhibiting Interleukin-8 Production: the Inhibition of Adenylate Cyclase," J Invest Dermatol, 117:284-293 (2001).
Karpiak et al., "Exogenous gangliosides enhance recovery from ens injury," Adv. Exp. Med. and Biol. 174: 489-497 (1984).
Kawai et al., "Structure of Biologically Active and Inactive Cerebrosides Prepared from Schizophyllum commune," 26:338-343 (1985).
Kells et al., "Glial-derived neurotrophic factor gene transfer for Parkinson's disease:anterograde distribution of AAV2 vectors in the primate brain," Neurobiol. Dis. 48: 228-235 (2012).
Kim et al., "Plasma Free Fatty Acids Decrease Insulin-Stimulated Skeletal Muscle Glucose Uptake by Suppressing Glycolysis in Conscious Rats," Diabetes, 45(4):446-453 (1996).
Koike et al., "Total synthesis of cerebrosides: (2S, 3R, 4E)-1-O-β-d-galactopyranosyl-N-(2'R and 2'S)-2'-hydroxytetracosanoylsphingenine," Carbohydrate Res, 162:237-246 (1987).
Kok et al., "Synthesis and biological evaluation of sulfur isosters of the potent influenza virus sialidase inhibitors 4-amino-4-deoxy- and 4-deoxy-4-guanidino-Neu5Ac2en," J Chem Soc Perkin Trans 1, 23:2811-2815 (1996).
Kordower et al., "Neurodegeneration prevented by lentiviral vector delivery of GDNF in primate models of Parkinson's disease," Science 290: 767-773 (2000).
Koster et al., "Hyperinsulinism induced by targeted suppression of beta cell KATP channels," PNAS, 99(26):16992-16997 (2002).
Kracun et al., "Gangliosides in the human brain development and aging," Neurochem Int. 20: 421-431 (1992).
Laemmli, "Cleavage of Structural Proteins during the Assembly of the Head of Bacteriophage T4," Nature, 227:680-685 (1970).
Laganiere et al., "An engineered zinc finger protein activator of the endogenous glial cell line-derived neurotrophic factor gene provides functional neuroprotection in a rat model of Parkinson's disease," J Neurosci, 30: 16469-16474 (2010).
Lang et al., "Randomized controlled trial of intraputamenal glial cell line-derived neurotrophic factor infusion in Parkinson disease," Ann. Neurol. 59: 459-466 (2006).
Langer, "New methods of drug delivery," Science, 249(4976):1527-1533 (1990).
Ledeen et al., "Gangliosides:structure, isolation, and analysis", Methods Enzymol, 83:139-191 (1982).
Ledeen, "Ganglioside structures and distribution: are they localized at the nerve ending?", J Cell Biol, 8(1):1-17 (1978).
Lees et al., "Modification of the Lowry procedure for the analysis of proteolipid protein," Anal. Biochem. 47: 184-192 (1972).
Mahadik et al., "Gangliosides in Treatment ofNeural Injury and Disease," Drug Development Res. 15: 337-360 (1988).

Marinier et al., "Sulfated Galactocerebrosides as Potential Antiinflammatory Agents," J Med Chem, 40(20):3234-3247 (1997).
Martinez et al., "GM1 specifically interacts with a-synuclein and inhibits fibrillation," Biochem. 46: 1868-1877 (2007).
Matsushita et al., "Adena-associated virus vectors can be efficiently produced without helper virus," Gene Ther. 5: 938-945 (1998).
Max et al., "GM3 (hematoside) sphingolipodystrophy", N Engl J Med, 291:929-931 (1974).
Mendoza et al., "Inhibition of Ligand-mediated HER2 Activation in Androgen-independent Prostate Cancer," Cancer Res, 62(19):5485-5488 (2002).
Michel., "Understanding Dopaminergic Cell Death Pathways in Parkinson Disease," Neuron Rev, 90: 675-691 (2016).
Misra et al., "Drug delivery to the central nervous system: a review," J Pharm Pharmaceut Sci, 6(2):252-273 (2003).
Miyagi et al., "Molecular cloning and characterization of a plasma membraneassociated sialidase specific for gangliosides," J. Biol. Chem. 274: 5004-5011 (1999).
Miyagi et al., "Plasma membrane—associated sialidase as a crucial regulator of transmembrane signalling", J Biochem, 144(3):279-285 (2008).
Mocchetti, "Exogenous gangliosides, neuronal plasticity and repair, and the neurotrophins," Cell Mol. Life Sci. 62: 2283-2294 (2005).
Morrison, "Polar Lipids in Bovine Milk," Biochim Biophys Acta, 176:537-546 (1969).
Murase et al., "A facile, regio- and stereo-selective synthesis of ganglioside GM3," Carbohydrate Res, 188:71-80 (1989).
Mutoh et al., "Ganglioside GM1 binds to the Trk protein and regulates receptor function," Proc. Natl. Acad. Sci. USA 92: 5087-5091 (1995).
Mutoh et al., "Stable transfection ofGM1 synthase gene into GM1-deficient NG108-15 cells, CR-72 cells, rescues the responsiveness of Trk-neurotrophin receptor to its ligand, NGF," Neurochem. Res. 27: 801-806 (2002).
Nadano et al., "A naturally occurring deaminated neuraminic acid, 3-deoxy-D-glycero-D-galacto-nonulosonic acid (KDN). Its unique occurrence at the nonreducing ends of oligosialyl chains in polysialoglycoprotein of rainbow trout eggs," J Biol Chem, 261:11550-11557 (1986).
Neville et al., "Analysis of fluorescently labeled glycosphingolipid-derived oligosaccharides following ceramide glycanase digestion and anthranilic acid labeling," Anal Biochem, 331(2):275-282 (2004).
Nojiri et al., "A specific type of ganglioside as a modulator of insulin-dependent cell growth and insulin receptor tyrosine kinase activity. Possible association of ganglioside-induced inhibition of insulin receptor function and monocytic differentiation induction in HL-60 cells," J Biol Chem, 266:4531-4537 (1991).
Oblinger et al., "Domain-dependent modulation of PDGFRbeta by ganglioside GM1", J Mol Neurosci, 20(2):103-113 (2003).
Ohmi et al., "Essential roles of gangliosides in the formation and maintenance of membrane microdomains in brain tissues," Neurochem Res. 37: 1185-1191(2012).
Ohshima et al., "Adrenalectomy reverses insulin resistance in muscle from obese (ob/ob) mice," Am J Physiol, 246(2):E193-E197 (1984).
Paratcha et al., "The neural cell adhesion molecule NCAM is an alternative signaling receptor for GDNF family ligands," Cell 113: 867-879 (2003).
Pascual et al., "Absolute requirement ofGDNF for adult catecholaminergic neuronsurvival," Nat. Neurosci. 11: 755-761 (2008).
Patel et al., "Intraputamenal infusion of glial cell line-derived neurotrophic factor in PD: a two-year outcome study," Ann. Neurol. 57: 298-302 (2005).
Paulsen et al., "Synthese der tetra- und trisaccharid-sequenzen von asialo-GM1 und -GM2. Lenkung der regioselektivität der glycosidierung von lactose," Carbohydrate Res., 137:39-62 (1985).
Pfaffli et al., "Thiglycosides Having 0-Benzyl Blocking Groups as Intermediates for the Systematic Sequential Synthesis of Oligiosaccharides. Synthesis of Isomaltose," Carbohydrate Res, 23:195-206 (1972).

(56) References Cited

OTHER PUBLICATIONS

Pierchala et al., "Glial cell line-derived neurotrophic factor-dependent recruitment of Ret into lipid rafts enhances signaling by partitioning Ret from proteasomedependent degradation," J Neurosci. 26: 2777-2787 (2006).
Pitto et al., "Influence of endogenous GM1 ganglioside on TrkB activity, in cultured neurons," FEBS Lett. 439: 93-96 (1998).
Ponpipom et al., "Synthesis of paragloboside analogs," Tetrahedron Lett, 19(20):1717-1720 (1978).
Pope-Coleman et al., "Effects of GM1 ganglioside treatment on pre- and postsynaptic dopaminergic markers in the striatum of parkinsonian monkeys", Synapse, 36(2):120-128 (2000).
Pope-Coleman., "Effects of Chronic Ganglioside Treatment on Cognitive and Motor Deficits in a Slowly Progressing Model of Parkinsonism in Non-Human Primates," Restor Neural Neurosci, 12(4): 255-256, (1998) abstract only.
Priem et al., "A new fermentation process allows large-scale production of human milk oligosaccharides by metabolically engineered bacteria," Glycobiol, 12(4):235-240 (2002).
Probert et al., "Chemoenzymatic synthesis of GM3, Lewis x and sialyl Lewis x oligosaccharides in 13C-enriched form," Tetrahedron Letters, 38(33):5861-8564 (1997).
Radin et al., "Metabolic effects of inhiting glucosylceramide synthesis with PDMP and other substances," Adv. Lipid Res. 26: 183-213 (1993).
Rangone et al., "The serum- and glucocorticoid-induced kinase SGK inhibits mutant huntingtin-induced toxicity by phosphorylating serine 421 of huntingtin", Eur J Neurosci, 19(2):273-279 (2004).
Rosenblad et al., "Intrastriatal glial cell line-derived neurotrophic factor promotes sprouting of spared nigrostriatal dopaminergic afferents and induces recovery of function in a rat model of Parkinson's disease," Neuroscience 82: 129-137 (1998).
Saito et al., "Gangliosides attenuate ethanol-induced apoptosis in rat cerebellar granule neurons", Neurochem Res, 24(9):1107-1115 (1999).
Schaade et al., "A membrane-located glycosphingolipid of monocyte/granulocyte lineage cells induces growth arrest and triggers the lytic viral cycle in Epstein-Barr virus genome-positive Burkitt lymphoma lines," Med Microbiol Immunol, 188(1):23-29 (1999).
Schneider et al., "A randomized, controlled, delayed start trial of GM1 ganglioside in treated Parkinson's disease patients," J Neurol. Sci. 324: 140-148 (2013).
Schneider et al., "GM1 ganglioside rescues substantia nigra pars compacta neurons and increases dopamine synthesis in residual nigrostriatal dopaminergic neurons in MPTP-treated mice," J Neurosci. Res. 42: 117-123 (1995).
Schneider et al., "GMl ganglioside in Parkinson's disease: Results of a five year open study," J. Neurol. Sci. 292: 45-51 (2010).
Schneider et al., "Recovery from experimental Parkinsonism in primates with GM1 ganglioside treatment," Science 256: 843-846 (1992).
Schneider et al., "Response of the damaged dopamine system to GM1 and semisynthetic gangliosides: effects of dose and extent of lesion," Neuropharmacology 34: 489-493 (1995).
Schwarzmann et al., "[26] Lysogangliosides: Synthesis and use in preparing labeled gangliosides," Meth Enzymol, 138:319-341 (1987).
Sciannamblo et al., "Changes of the ganglioside pattern and content in human fibroblasts by high density cell population subculture progression", Glycoconj J, 19(3):181-186 (2002).
Segler-Stahl et al., "Changes in the concentration and composition of human brain gangliosides with aging," Gerontology 29: 161-168 (1983).
Seyfried et al., "Ganglioside GD3: structure, cellular distribution, and possible function", Mol Cell Biochem, 68(1):3-10 (1985).
Sheikh et al., "Mice lacking complex gangliosides develop Wallerian degeneration and myelination defects", PNAS, 96(13):7532-7537 (1999).
Simpson et al., "Infantile-onset symptomatic epilepsy syndrome caused by a homozygous loss-of-function mutation of GM3 synthase", Nat Genet, 36:1225-1229 (2004).

Sipione et al., "Early transcriptional profiles in huntingtin-inducible striatal cells by microarray analyses", Hum Mol Genet, 11(17):1953-1965 (2002).
Skaper et al., "Ganglioside function in the development and repair of the nervous system. From basic science to clinical application," Mol. Neurobiol. 3: 173-199 (1989).
Slevin et al., "Improvement of bilateral motor functions in patients with Parkinson disease through the unilateral intraputaminal infusion of glial cell line-derived neurotrophic factor," J Neurosurg. 102: 216-222 (2005).
Slow et al., "Selective striatal neuronal loss in a YAC128 mouse model of Huntington disease", Hum Mol Genet, 12(13):1555-1567 (2003).
Sogin et al., "Binding of cytochalasin B to human erythrocyte glucose transporter," Biochem, 19(23):5417-5420 (1980).
Song et al., "Expression of full-length polyglutamine-expanded Huntingtin disrupts growth factor receptor signaling in rat pheochromocytoma (PC12) cells", J Biol Chem, 277:6703-6707 (2002).
Sonnio et al., "Gangliosides as components of lipid membrane domains", Glycobiology, 17:1R-13R (2007).
Steppan et al., "The hormone resistin links obesity to diabetes," Nature, 409:307-312 (2001).
Stine et al., "Correlation between the onset age of Huntington's disease and length of the trinucleotide repeat in IT-15", Hum Mol Genet, 2(10):1547-1549 (1993).
Sun et al., "Myelin-associated glycoprotein (Siglec-4) expression is progressively and selectively decreased in the brains of mice lacking complex gangliosides", Glycobiology, 14(9):851-857 (2004).
Suzuki et al., "Gangliosides as influenza virus receptors. Variation of influenza viruses and their recognition of the receptor sialo-sugar chains," Prog Lipid Res, 33(4):429-457 (1994).
Svennerholm et al., "Membrane lipids of adult human brain: lipid composition of frontal and temporal lobe in subjects of age 20 to 100 years," J Neurochem. 63: 1802-1811 (1994).
Svennerholm, "Quantitative estimation of sialic acids. II. A colorimetric resorcinol-hydrochloric acid method", Biochim Biophys Acta, 24:604-611 (1957).
Svennholm et al., "A procedure for the quantitative isolation of brain gangliosides," Biochim Biophys Acta, 617:97-109 (1980).
Tansey et al., "GFRalpha-mediated localization of RET to lipid rafts is required for effective downstream signaling, differentiation, and neuronal survival," Neuron 25: 611-623 (2000).
Tapley et al., "K252a is a selective inhibitor of the tyrosine protein kinase activity of the trk family of oncogenes and neurotrophin receptors", Oncogene, 7:371-381 (1992).
Tettamanti et al., "Sub-synaptosomal localization of brain particulate neuraminidose", Brain Res, 47(2):515-518 (1972).
Tettamanti, "Ganglioside/glycosphingolipid turnover: new concepts", Glycoconj J, 20(5):301317 (2004).
The Mereck Manual, 16th edition, 1992, pp. 2657, 1466-71,1464-65,1518-19.
Toledo et al., "Effect of ganglioside and tetraspanins in microdomains on interaction of integrins with fibroblast growth factor receptor", J Biol Chem, 280(16):16277-16234 (2005).
Tomac et al., "Protection and repair of the nigrostriatal dopaminergic system by GDNF in vivo," Nature. 373: 335-339 (1995).
Trester, Cognitive Impairment, Parkinson's Disease Foundation, http://www.pdf.org/en/cognitive_impairment_pd, published Jan. 5, 2011.
Trettel et al., "Dominant phenotypes produced by the HD mutation in STHdh(Q111) striatal cells", Hum Mol Genet, 9(19):2799-2809 (2000).
Trupp et al., "Complementary and overlapping expression of glial cell line-derived neurotrophic factor (GDNF), c-ret proto-oncogene, and GDNF receptor-alpha indicates multiple mechanisms of trophic actions in the adult rat CNS," J Neurosci. 17: 3554-3567 (1997).
Tsujihara,"A New Class of Nitrosoureas. II. Synthesis and Antitumor Activity of 1-(2-Chloroethyl)-3, 3-disubstituted-1-nitrosoureas having a Glucopyranosyl, Mannopyranosyl or Galactopyranosyl Moiety," Chem Pharm Bull, 29(11):3262-3273 (1981).
Varki, "Diversity in the sialic acids," Glycobiol, 2:25-40 (1992).

(56) References Cited

OTHER PUBLICATIONS

Vaughan et al., "Glycosynthase-Mediated Synthesis of Glycosphingolipids," J Am Chem Soc, 128(19):6300-6301 (2006).
Vucic et al., "Guillain-Barre syndrome: an update", J Clin Neurosci, 16(6):733-741 (2009).
Vyas et al., "Gangliosides are functional nerve cell ligands for myelin-associated glycoprotein (MAG), an inhibitor of nerve regeneration", PNAS, 99(12):8412-8417 (2002).
Wade et al., "Atrophy and degeneration in sciatic nerve of presymptomatic mice carrying the Huntington's disease mutation", Brain Res, 1188:61-68 (2008).
Walker, "Huntington's disease", Lancet, 369(9557):218-228 (2007).
Wang et al., "Brain ganglioside and glycoprotein sialic acid in breastfed compared with formula-fed infants," Am J Clin Nutr, 78(5):1024-1029 (2003).
Wang et al., "Sialic Acid Concentration of Brain Gangliosides: Variation Among Eight Mammalian Species," Comp Biochem Physiol A Mol Integr Physiol, 119:435-439 (1998).
Warby et al., "Huntingtin phosphorylation on serine 421 is significantly reduced in the striatum and by polyglutamine expansion in vivo", Hum Mol Genet, 14(11):1569-1577 (2005).
Warby et al., "Phosphorylation of huntingtin reduces the accumulation of its nuclear fragments", Mol Cell Neurosci, 40(2):121-127 (2009).
Watanabe et al., "Ganglioside GM3 Overexpression Induces Apoptosis and Reduces Malignant Potential in Murine Bladder Cancer," Cancer Res, 62:3850-3854 (2002).
Wieraszko et al., "The role of monosialoganglioside GM1 in the synaptic plasticity: in vitro study on rat hippocampal slices", Brain Res, 345(1):159-164 (1985).
Wright et al., "Recombinant adeno-associated virus: formulation challenges and strategies for a gene therapy vector," Curr. Opin. Drug Discov. 6: 174-178 (2003).
Wu et al., "Cerebellar neurons lacking complex gangliosides degenerate in the presence of depolarizing levels of potassium," Proc. Natl. Acad. Sci. USA 98: 307-312 (2001).
Wu et al., "Deficiency of ganglioside GM1 correlates with Parkinson's disease in mice and humans," J Neurosci. Res. 90: 1997-2008 (2012).
Wu et al., "Enhanced susceptibility to kainate-induced seizures, neuronal apoptosis and death in mice lacking gangliotetraose gangliosides. Protection by LIGA 20, a permeant analog of GM1," J. Neurosci. 25: 11014-11022 (2005).
Wu et al., "Ganglioside GM1 deficiency in effector T cells from NOD mice induces resistance to regulatory T-cell suppression," Diabetes 60: 2341-2349 (2011).
Wu et al., "Induction of calcium influx through TRPC5 channels by cross-linking of GM1 ganglioside associated with alpha5beta1 integrin initiates neurite outgrowth", J Neurosci, 27(28):7447-7458 (2007).
Wu et al., "Mice Lacking Major Brain Gangliosides Develop Parkinsonism," Neurochem. Res. 36: 1707-1714 (2011).
Wu et al., "Mutant NG108-15 cells (NG-CR72) deficient in GM1 synthase respond aberrantly to axonogenic stimuli and are vulnerable to calcium-induced apoptosis: they are rescued with Liga-20," J. Neurochem. 76: 690-702 (2001).
Wu et al., "New findings on nuclear gangliosides: overview on metabolism and function," J. Neurochem. 116: 714-720 (2011).
Wu et al., "Sodium-calcium exchanger complexed with GM1 ganglioside in nuclear membrane transfers calcium from nucleoplasm to endoplasmic reticulum," Proc. Natl. Acad. Sci. USA 106: 10829-10834 (2009).
Wu et al., "Susceptibility of cerebellar granule neurons from GM2/GD2 synthase-null mice to apoptosis induced by glutamate excitotoxicity and elevated KCl: rescue by GM1 and LIGA20", Glycoconj J, 21(6):305-313 (2004).
Xia et al., "Characterization of the promoter and the transcription factors for the mouse UDP-Ga:betaGcNAc beta1,3-galactosyltransferase gene", Gene, 309(2):117-123 (2003).

Xie et al., "Potentiation of a sodium-calcium exchanger in the nuclear envelope by nuclear GM1 ganglioside," J. Neurochem. 81: 1185-1195 (2002).
Yamada et al., "Retinoic acid induces functional c-Ret tyrosine kinase in human neuroblastoma," NeuroReport. 18: 359-363 (2007).
Yang et al., "Akt/protein kinase B signaling inhibitor-2, a selective small molecule inhibitor of Akt signaling with antitumor activity in cancer cells overexpressing Akt", Cancer Res, 64(13)4394-4399 (2004).
Yarnall et al., "Parkinson's disease," Medicine, 40(10):529-535 (2012).
Yoon et al., "Epidermal growth factor receptor tyrosine kinase is modulated by GM3 interaction with N-linked GlcNAc termini of the receptor", PNAS, 103(50):18987-18991 (2006).
Yoshikawa et al., "Aroma Glycosides from Hovenia Dulsis," Phytochem, 34(5):1431-1433 (1993).
Yu et al., "Regulation of ganglioside biosynthesis in the nervous system", J Lipid Res, 45:783-793 (2004).
Yu et al., "The role of glycosphingolipid metabolism-in the developing brain", J Lipid Res, 50:S440-S445 (2009).
Zala et al., "Phosphorylation of mutant huntingtin at S421 restores anterograde and retrograde transport in neurons", Hum Mol Genet, 17(24):3837-3846 (2008).
Zehavi et al., "Enzymic Glycosphingolipid Synthesis on Polymer Supports. II. Synthesis of Lactosyl Ceramide," Glycoconjugate J, 7(3):229-234 (1990).
Zhang et al., "Inhibitory action of ganglioside GM3 on murine neuroblastoma cell proliferation: modulating effect of fetal calf serum," Anticancer Res, 15(3):661-666 (1995).
Zuccato et al., "Loss of huntingtin-mediated BDNF gene transcription in Huntington's disease", Science, 293(5529):493-498 (2001).
Alpaugh et al., "Disease-modifying effects of ganglioside GM1 in Huntington's disease models," EMBO Mol Med, 9(11):1537-1557 (2017).
Angeleri et al., "GM1 Ganglioside Therapy in Acute Ischemic Stroke," Cerebrovascular Dis, 2:163-68 (1992).
Antoine et al., "Large-scale in vivo synthesis of the carbohydrate moieties of gangliosides GM1 and GM2 by metabolically engineered *Escherichia coli*," Chembiochem, 4(5):406-412 (2003).
Argentino et al., "GM1 ganglioside therapy in acute ischemic stroke. Italian Acute Stroke Study—Hemodilution + Drug," Stroke 20(9):1143-9 (1989).
Augustinsson et al., "Intracerebroventricular administration of GM1 ganglioside to presenile Alzheimer patients," Dement Geriatr Cogn Disord, 8(1):26-33 (1997).
Aykutlu et al., "No association of anti-GM1 and anti-GAD antibodies with juvenile myoclonic epilepsy: a pilot study," Seizure, 14(5):362-366 (2005).
Barros et al., "The Effect of Monosialoganglyoside (GM-1) Administration in Spinal Cord Injury," Acta Ortop Bras, 24(3):123-126 (2016).
Bassi et al., "Double-blind evaluation of monosialoganglioside (GM1) therapy in stroke," J Neurosci Res, 12(2-3):493-498 (1984).
Boccuto et al., "A mutation in a ganglioside biosynthetic enzyme, ST3GAL5, results in salt & pepper syndrome, a neurocutaneous disorder with altered glycolipid and glycoprotein glycosylation," Hum Mol Genet, 23(2):418-433 (2014).
Caughlin et al., "Age-dependent and regional heterogeneity in the long-chain base of a-series gangliosides observed in the rat brain using MALDI Imaging," Sci Rep, 7(1):16135 (2017).
Chentanez et al., "Ganglioside GM1 (porcine) ameliorates paclitaxel-induced neuropathy in rats," J Med Assoc Thai, 92(1):50-57 (2009).
Coombs et al., "Neurotoxicology of chronic infusion of the ganglioside GM1 in the ewe: phase I. intrathecal administration," Anesth Analg, 77(3):507-15 (1993).
Cornelli et al., "Pharmacokinetics of GM1 ganglioside following parenteral administration," J Pharm Pharmacol, 42(10):708-11 (1990).
Daniotti et al., "Metabolic pathways and intracellular trafficking of gangliosides," IUBMB Life, 63(7):513-520 (2011).
Di Pardo et al., "Ganglioside GM1 induces phosphorylation of mutant huntingtin and restores normal motor behavior in Huntington disease mice," Proc Natl Acad Sci, 109(9):3528-3533 (2012).

(56) References Cited

OTHER PUBLICATIONS

Forsayeth et al., "Ganglioside Metabolism and Parkinson's Disease," Front Neurosci, 12:45 (2018).
Fragaki et al., "Refractory epilepsy and mitochondrial dysfunction due to GM3 synthase deficiency," Eur J Hum Genet, 21(5):528-534 (2013).
Furukawa et al., "Glycosphingolipids in engineered mice: insights into function," Semin Cell Dev Biol, 15:389-396 (2004).
Furukawa et al., In: Comprehensive Glycoscience from Chemistry to Systems Biology, vol. 4. Kamerling JP, Boons GJ, editors. Oxford, UK: Elsevier; 2007. Knockout mice and glycolipids; pp. 149-157.
Geisler et al., "Recovery of motor function after spinal-cord injury—a randomized, placebo-controlled trial with GM-1 ganglioside," N Engl J Med, 324(26):1829-38 (1991).
Geisler et al., "The Sygen multicenter acute spinal cord injury study," Spine, 26(24 Suppl):S87-98 (2001).
Geisler, "Gangliosides, Novel therapies for CNS injuries. Rationales and Results," 1st Ed. Peterson PL and Phillis JW, editors. CRC Press, pp. 291-310 (1996).
Ghidoni et al., "Incorporation and metabolism of exogenous GM1 ganglioside in rat liver," Biochem J, 237:147-155 (1986).
Ghidoni et al., "Uptake, cell penetration and metabolic processing of exogenously administered GM1 ganglioside in rat brain," Neurochem Int, 15(4):455-465 (1989).
Giraldi et al., "A pilot study with monosialoganglioside GM1 on acute cerebral ischemia," Acta Neurol (Napoli), 12(3):214-21 (1990).
Granieri et al., "Ganglioside therapy and Guillain-Barré syndrome. A historical cohort study in Ferrara, Italy, fails to demonstrate an association," Neuroepidemiology, 10(4):161-169 (1991).
Grieco et al., "Evaluating neuroprotective agents for clinical anti-ischemic benefit using neurological and neuropsychological changes after cardiac surgery under cardiopulmonary bypass. Methodological strategies and results of a double-blind, placebo-controlled trial of GM1 ganglioside," Stroke, 27(5):858-74 (1996).
Hadaczek et al., "GDNF signaling implemented by GM1 ganglioside; failure in Parkinson's disease and GM1-deficient murine model," Exp Neurol, 263:177-89 (2015).
Heywood et al., "The toxicology of a ganglioside extract (Cronassial)," Toxicol Lett, 15(4):275-82 (1983).
Hoffbrand et al., "Trial of ganglioside GM1 in acute stroke," J Neurol Neurosurg Psychiatry, 51(9):1213-4 (1988).
Holford et al., "A pharmacokinetic standard for babies and adults," J Pharm Sci, 102(9):2941-52 (2013).
Human Gene Mutation Database, Institute of Medical Genetics, Cardiff University, http://www.hgmd.cf.ac.uk/ac/index.php.
Hungund et al., "Placental transfer of (3H)-GM1 and its distribution to maternal and fetal tissues of the rat," Life Sci, 53(2):113-119 (1993).
Kastner et al., "Decreased tyrosine hydroxylase content in the dopaminergic neurons of MPTP-intoxicated monkeys: effect of levodopa and GM1 ganglioside therapy," Annals of Neurology, 36(2):206-14 (1994).
Kittaka et al., "Impaired hypoglossal nerve regeneration in mutant mice lacking complex gangliosides: down-regulation of neurotrophic factors and receptors as possible mechanisms," Glycobiology, 18:509-516 (2008).
Landi et al., "Guillain-Barré syndrome after exogenous gangliosides in Italy," BMJ, 307:1463-1464 (1993).
Lardone et al., "Unusual presence of anti-GM1 IgG-antibodies in a healthy individual, and their possible involvement in the origin of disease-associated anti-GM1 antibodies," J Neuroimmunol, 173(1-2):174-9 (2006).
Ledeen et al., "Gangliosides of the Nervous System," Methods Mol Biol, 1804:19-55 (2018).
Ledeen et al., "The multi-tasked life of GM1 ganglioside, a true factotum of nature," Trends Biochem Sci, 40(7):407-418 (2015).
Lee et al., "GM3 synthase deficiency due to ST3GAL5 variants in two Korean female siblings: Masquerading as Rett syndrome-like phenotype," Am J Med Genet A, 170(8):2200-2205 (2016).
Lenzi et al., "Early treatment of stroke with monosialoganglioside GM-1. Efficacy and safety results of the Early Stroke Trial," Stroke, 25(8):1552-8 (1994).
Li et al., "Chapter Two—Congenital Disorders of Ganglioside Biosynthesis," Progress in Molecular Biology and Translational Science, 156:63-82 (2018).
Menalled et al., "Time course of early motor and neuropathological anomalies in a knock-in mouse model of Huntington's disease with 140 CAG repeats," J Comp Neurol, 465(1):11-26 (2003).
Mitchell et al., "Transfer of gangliosides across the human placenta," Placenta, 33(4):312-316 (2012).
NIH US National Library of Medicine, Genetics Home Reference: GM3 Synthase Deficiency. 2018. Website. https://ghr.nlm.nih.gov/condition/gm3-synthase-deficiency.
Niimi et al., "Improvement of spontaneous alternation behavior deficit by activation of alpha4beta2 nicotinic acetylcholine receptor signaling in the ganglioside GM3-deficient mice," Biomed Res, 34(4):189-195 (2013).
Orphanet Report Series, "Prevalence and incidence of rare diseases: Bibliographic data," Rare Diseases Collection, No. 2, (last accessed Sep. 5, 2019). http://www.orpha.net/orphacom/cahiers/docs/GB/Prevalence_of_rare_diseases_by_decreasing_prevalence_or_cases.pdf.
Palestini et al., "Lack of the ganglioside molecular species containing the C20-long-chain bases in human, rat, mouse, rabbit, cat, dog, and chicken brains during prenatal life," J Neurochem, 56(6):2048-2050 (1991).
Q3D Elemental Impurities, Guidance for Industry, ICH, Sep. 2015. https://www.fda.gov/Drugs/GuidanceComplianceRegulatoryInformation/Guidances/default.htm.
Rebbaa et al., "Distribution of exogenously added gangliosides in serum proteins depends on the relative affinity of albumin and lipoproteins," J Lipid Res, 36(3):564-572 (1995).
Roberts et al., "Iatrogenic hyperlipidaemia with GM1 ganglioside," Lancet, 342(8863):115 (1993).
Rost et al., "Multiple-dose pharmacokinetics of ganglioside GM1, after intravenous and intramuscular administration to healthy volunteers," Clin Pharmacol Ther, 50(2):141-149 (1991).
Ryu et al., Attenuation of cortical neuronal apoptosis by gangliosides. J Pharmacol Exp Ther, 290(2):811-6 (1999).
SASS Study Group, "Ganglioside GM1 in acute ischemic stroke:The SASS Trial," Stroke, 25(6):1141-1148 (1994).
Saul et al., "'Salt-and-pepper' pigmentary changes with severe mental retardation: a new neurocutaneous syndrome?," Proc Greenwood Genet Center, 2:6-9 (1983).
Schengrund, "The role(s) of gangliosides in neural differentiation and repair: a perspective," Brain Res Bull, 24:131-141 (1990).
Schnaar, "Gangliosides of the vertebrate nervous system," J Mol Biol, 428(16):3325-3336 (2016).
Schneider et al., "GM1 ganglioside in Parkinson's disease: Pilot study of effects on dopamine transporter binding," J Neurol Sci. 356(1-2):118-123 (2015).
Schneider et al., "GM1 ganglioside treatment of Parkinson's disease: an open pilot study of safety and efficacy," Neurology. 45(6):1149-1154 (1995).
Schneider et al., "Parkinson's disease: improved function with GM1 ganglioside treatment in a randomized placebo-controlled study," Neurology. 50(6):1630-1636 (1998).
Schneider JS, "Gangliosides and Glycolipids in Neurodegenerative Disorders,". In: Yu RK, Schengrund CL, editors. Glycobiology of the Nervous System. New York, NY: Springer New York; pp. 449-461, (2014).
Sheng et al., "Adjuvant treatment with monosialoganglioside may improve neurological outcomes in neonatal hypoxic-ischemic encephalopathy: A meta-analysis of randomized controlled trials," PloS one. 12(8):e0183490 (2017).
Sonnino et al., "Ganglioside molecular species containing C18- and C20-sphingosine in mammalian nervous tissues and neuronal cell cultures," Biochim Biophys Acta, 1469(2):63-77 (2000).
Sugiura et al., "Imaging Mass Spectrometry Technology and Application on Ganglioside Study; Visualization of Age-Dependent Accumulation of C20-Ganglioside Molecular Species in the Mouse Hippocampus," PLoS ONE. 3(9):e3232 (2008).

(56) References Cited

OTHER PUBLICATIONS

Svennerholm et al., "Parenteral administration of GM1 ganglioside to presenile Alzheimer patients," Acta Neurol Scand, 81(1):48-53 (1990).

Takamiya et al., "Mice with disrupted GM2/GD2 synthase gene lack complex gangliosides but exhibit only subtle defects in their nervous system," Proc Natl Acad Sci U S A. 93(20):10662-10667 (1996).

Tettamanti et al., "Salvage pathways in glycosphingolipid metabolism," Biochemie. 85:423-437 (2003).

Valsecchi et al., "Age-related changes of the ganglioside long-chain base composition in rat cerebellum," Neurochem Int. 28(2):183-187 (1996).

Valsecchi et al., "Changes in the ganglioside long-chain base composition of rat cerebellar granule cells during differentiation and aging in culture," J Neurochem. 60(1):193-196 (1993).

Wang et al., "Cutaneous dyspigmentation in patients with ganglioside GM3 synthase deficiency," Am J Med Genet A. 161A(4):875-879 (2013).

Wang et al., "Early growth and development impairments in patients with ganglioside GM3 synthase deficiency," Clin Genet. 89(5):625-629 (2016).

Wu et al., "Mice deficient in GM1 manifest both motor and non-motor symptoms of Parkinson's Disease; successful treatment with synthetic GM1 ganglioside," Manuscript in preparation. (2018).

Yoshikawa et al., "Mice lacking ganglioside GM3 synthase exhibit complete hearing loss due to selective degeneration of the organ of Corti," Proc Natl Acad Sci U S A. 106(23):9483-9488 (2009).

Yuki et al. "A bacterium lipopolysaccharide that elicits Guillain-Barré syndrome has a GM1 ganglioside-like structure," J Exp Med. 178:1771-1775 (1993).

Yuki et al. "Carbohydrate mimicry between human ganglioside GM1 and Campylobacter jejuni lipooligosaccharide causes Guillain-Barre syndrome," Proc Natl Acad Sci U S A. 101(31):11404-11409 (2004).

Zhu et al. "Clinical effects of Ganglioside and fructose-1,6-diphosphate on neonatal heart and brain injuries after Asphyxia," Pak J Med Sci. 33(5):1199-1204 (2017).

Zhu et al. "Ganglioside-monosialic acid (GM1) prevents oxaliplatin-induced peripheral neurotoxicity in patients with gastrointestinal tumors," World J Surg Oncol. 11:19 (2013).

Zhu et al. "Influence of one-year neurologic outcome of treatment on newborns with moderate and severe hypoxic-ischemic encephalopathy by rhuEPO combined with ganglioside (GM1)," Eur Rev Med Pharmacol Sci. 19(20):3955-3960 (2015).

\* cited by examiner

GLYCOLIPIDS AS TREATMENT FOR DISEASE

CROSS-REFERENCES TO RELATED APPLICATIONS

This application is a continuation of U.S. patent application Ser. No. 13/260,553, filed Sep. 26, 2011, which is a U.S. National Phase Entry under 35 U.S.C. 371 of International Application No. PCT/US10/28725, filed Mar. 25, 2010, which claims priority under 35 U.S.C. § 119(e) to U.S. Provisional Patent Application No. 61/163,371, filed on Mar. 25, 2009, U.S. Provisional Patent Application No. 61/293,200, filed Jan. 7, 2010, U.S. Provisional Patent Application No. 61/244,735, filed Sep. 22, 2009, U.S. Provisional Patent Application No. 61/220,151, filed Jun. 24, 2009, U.S. Provisional Patent Application No. 61/180,346, filed May 21, 2009 and U.S. Provisional Patent Application No. 61/180,098, filed May 20, 2009, which are incorporated herein by reference in their entirety for all purposes.

FIELD OF THE INVENTION

This invention relates to methods of treating and amliorating diseases of cancer, hyperinsulinemia, hypoglycemia and atypical parkinson's disease, tauopathies, and other neurological diseases, and/or a ganglioside deficiency state or disorder by administering a suitable glycolipid, ganglioside or ganglioside analog.

BACKGROUND OF THE INVENTION

Besides the administration of antibodies or tyrosine kinase inhibitors for malignancies, the typical treatment for many cancers is the administration of radiation therapy and chemotherapeutic agents. However, side effects are a limiting factor in radiation treatments. Combination chemotherapy has some success in reaching partial or complete responses. Unfortunately, the remissions obtained through chemotherapy are often not durable.

Congenital hyperinsulinism (CHI, OMIM 256450) is a genetic disorder of pancreatic β-cell function characterized by failure to suppress insulin secretion in the presence of hypoglycemia, resulting in brain damage or death if inadequately treated.

Neuroendocrine tumors including such cancers as insulinoma, hepatomas, mesotheliaoma and fibrosarcoma may also cause hyperinsulinemia accompanied by hypoglycemia.

Gangliosides are sialic acid containing glycosphingolipids. Gangliosides are normal components of plasma membranes which are particularly abundant in the nervous system. In humans, gangliosides are most abundant in the gray matter of the brain, particularly in nerve endings. As a result, the addition of one or more glycolipids for cancer (e.g., during immunotherapy, such as antibodies or tyrosine kinase inhibitors), patients suffering from hyperinsulinemia, hypoglycemia or hypersinsulinemia with hypoglycemia or neurological disorders (e.g., Huntington's Disease, multiple systems atrophy, atypical Parkinson's disease, tauopathies) may reduce the mortality and/or morbidities associated with each disease. Attempts have been made to use gangliosides in the treatment of disorders of the nervous system. This has led to the development of synthetic gangliosides as well as natural ganglioside containing compositions for use in the treatment of disorders of the nervous system (see, U.S. Pat. Nos. 4,476,119; 4,593,091; 4,639,437; 4,707,469; 4,713,374; 4,716,223; 4,849,413; 4,940,694; 5,045,532; 5,135,921; 5,183,807; 5,190,925; 5,210,185; 5,218,094; 5,229,373; 5,260,464; 5,264,424; 5,350,841; 5,424,294; 5,484,775; 5,519,007; 5,521,164; 5,523,294; 5,677,285; 5,792,858; 5,795,869; and 5,849,717).

There exists a need in the art for ganglioside compounds and methods of treatment which use the compounds to treat diseases such as cancer, hyperinsulinemia, atypical Parkinson's disease, multiple systems atrophy, Huntington's disease, tauopathies or ganglioside deficient states or disorders, including neurological conditions. Ideally, such compounds act in a manner similar to, or better than, the natural gangliosides for the prophylaxis, treatment and cure of such states or disorders.

BRIEF SUMMARY OF THE INVENTION

In various aspects, this invention provides compounds, compositions, and methods for treating congenital and non-congenital diseases. Exemplary diseases treatable according to the invention include those characterized by ganglioside deficiency. Exemplary diseases treatable according to the invention include cancer (e.g., in combination with one or more of antibodies, antibody fragments and antibody conjugates, tyrosine kinase inhibitors), atypical Parkinson's disease, Parkinson's Disease, other neurological diseases and conditions (e.g., multiple systems atrophy, Huntington's disease, GM3 synthase deficiency, GM2 synthase deficiency); a tauopathy (e.g., a neurological disorder or condition associated with an increased aggregation of tau protein), hyperinsulinemia, hypoglycemia or hyperinsulinemia with hypoglycemia.

In a first aspect, the invention provides novel synthetic compositions of formula (1)-(5):

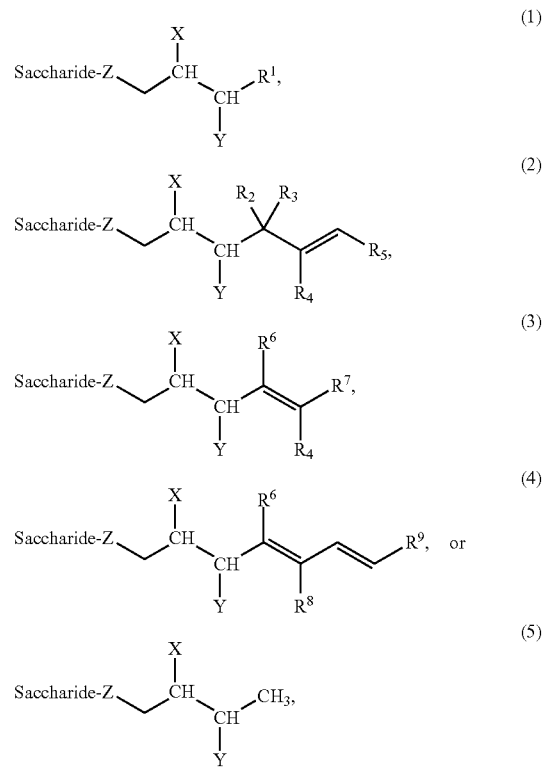

including pharmaceutically acceptable salts, isomers, hydrates, solvates, and prodrugs thereof in which Z can be O, S, C($R^{10}$)$_2$ and $NR^2$, X can be H, D, —$OR^{11}$, —$NR^{11}R^{12}$, —$SR^{11}$, and —$CHR^{11}R^{12}$, and $R^{10}$, $R^{11}$ and $R^{12}$ can be independently selected from H, D, substituted or unsubstituted alkyl, substituted or unsubstituted heteroalkyl, substituted or unsubstituted aryl, substituted or unsubstituted heteroaryl, substituted or unsubstituted heterocycloalkyl, —C(=B)$R^{13}$, —C(=B)-Z-$R^{13}$, —$SO_2R^{13}$, and —$SO_3$ functional moieties. Further, a novel ganglioside of the present invention can have B, B', and Z independently selected from O, $NR^{14}$ or S, and Y can be selected from H, D, —$OR^{15}$, —$SR^{15}$, —$NR^{15}R^{16}$, substituted or unsubstituted alkyl, substituted or unsubstituted heteroalkyl, substituted or unsubstituted aryl, substituted or unsubstituted heteroaryl, and substituted or unsubstituted heterocycloalkyl moieties. Further still, a novel ganglioside of the invention can have $R^1$, $R^2$, $R^3$, $R^4$, $R^5$, $R^6$, $R^7$, $R^8$, $R^9$, $R^{13}$, $R^{14}$, independently selected from H, D, —$OR^{17}$, —$NR^{17}R^{18}$, —$SR^{19}$, and —$CHR^{19}R^{20}$, substituted or unsubstituted alkyl, substituted or unsubstituted heteroalkyl, substituted or unsubstituted aryl, substituted or unsubstituted heteroaryl, substituted or unsubstituted heterocycloalkyl moieties. Further $R^{15}$, $R^{16}$, $R^{17}$, $R^{18}$, and $R^{19}$ are independently selected from substituted or unsubstituted alkyl, substituted or unsubstituted heteroalkyl, substituted or unsubstituted aryl, substituted or unsubstituted heteroaryl, substituted or unsubstituted heterocycloalkyl moieties, —C(=B')$R^{20}$, —C(=B')-Z—$R^{20}$, —$SO_2R^{20}$, and —$SO_3$ functional moieties. Further, $R^{20}$ is selected from H, D, —$OR^{21}$, —$SR^{21}$, —$NR^{21}R^{22}$, substituted or unsubstituted alkyl, substituted or unsubstituted heteroalkyl, substituted or unsubstituted aryl, substituted or unsubstituted heteroaryl, substituted or unsubstituted heterocycloalkyl moieties. Further, $R^{21}$ and $R^{22}$ are independently selected from H, D, substituted or unsubstituted alkyl, substituted or unsubstituted heteroalkyl, substituted or unsubstituted aryl, substituted or unsubstituted heteroaryl, substituted or unsubstituted heterocycloalkyl moieties. Further, double bonds can be E, Z or a mixture of E and Z.

In some embodiments in which X is NHR that contains an amide (i.e., R is hydrogen), a substituted or unsubstituted fatty acid amide of from 1 to 40 carbon atoms in length or from 2 to 40 carbon atoms in length or C(O)CHCl$_2$; saccharide is a moiety of a naturally occurring mammalian ganglioside or glycosphingolipid or sulfatide; Y is substituted or unsubstituted alkyl, alkenyl, or alkynyl from 12 to 40 carbon atoms in length; and R''' is hydrogen or hydroxy. In some embodiments, the Y member is unsubstituted. In some embodiments, the Y member consists of an unsubstituted linear or branched alkyl chain or an unsubstituted linear or branched alkenyl chain. In some embodiments, the Y member is alkenyl having from 2 to 4 double bonds in a branched or linear carbon chain. In some embodiments, the R fatty acid is unsubstituted. In other embodiments, the R fatty acid member is from 14 to 24 carbon atoms in length. In some exemplary embodiments, the R fatty acid is unsubstituted and the Y member consists of an unsubstituted linear or branched alkyl chain or an unsubstituted linear or branched alkenyl chain. In a further set of such embodiments, R is a long chain saturated or polyunsaturated fatty acid; in some further embodiments the long chain polyunsaturated fatty acid is DHA, EPA, or GLA. In some embodiments of the above, R is an α-hydroxy fatty acid (e.g., α-hydroxy palmitic acid) joined at the amide bond to the sphingoid base. In some embodiments, R is a α-hydroxy fatty acid (e.g., α-hydroxy palmitic acid) joined at the amide bond to a 4,8-sphingadiene base of from 16, 18 or 20 carbons in length.

In other embodiments of any of the above, the saccharide moiety is selected from galactosyl glycosphingolipids, digalactosyl glycosphingolipids, sulfated glycosphingolipids, glucosyl glycosphingolipids, lactosyl glycosphingolipids, the lacto series glycosphingolipids, the neo-lacto series of glycosphingolipids, globoside glycosphingolipids, or the ganglioside glycosphingolipids (Chen, "Handbook of Carbohydrate Engineering", Chapter 1, pages 1-48, CRC Press, Yarema, ed., (2005)). In preferred embodiments, the saccharide moiety is a glycosphingolipid selected from GA2, GA1, GM1b, GD1c, GD1α, GM3, GM2, GM4, GM1a, GD1a, GT1a, GT1α, GD3, GD2, GD1b, GT1b, GQ1b, GQ1bα, GT3, GT2, GT1c, GQ1c, GP1c, sulfatide, globoside, sialyl paragloboside and GP1cα. In a particularly preferred embodiment, the compound is the ganglioside GM1 or another compound of the above formula having the saccharide moiety of GM1. In other embodiments, the compound is the ganglioside GM3 or GD3 or another compound of the above formula having the saccharide moiety of GM3 or GD3. In still other embodiments, the compound or its saccharide moiety corresponds to that of GT1b, sulfatide, or, more preferably, Gb3.

In some exemplary embodiments, the present invention also provides a novel ganglioside compound in which the saccharide component can be

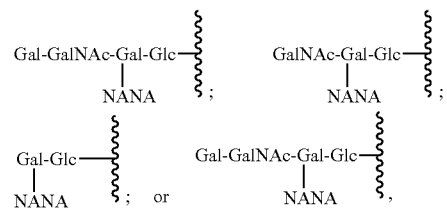

and such saccharide moieties may or may not be deacetylated. These structures are optionally incorporated into the compounds of formulae 1-5, above.

The invention further provides pharmaceutical compositions including at least one compound of the invention and a pharmaceutically acceptable carrier.

In some exemplary embodiments of any of the above, the compound is of formula (6)-(10):

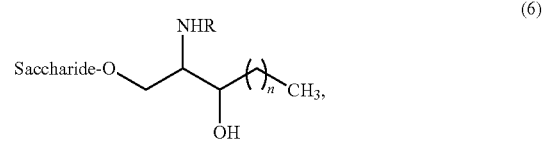

(6)

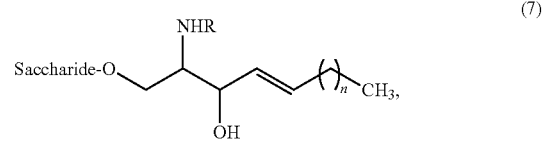

(7)

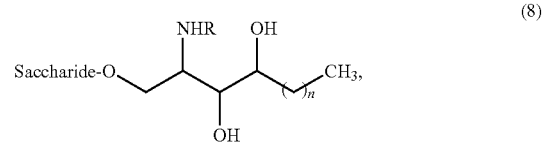

(8)

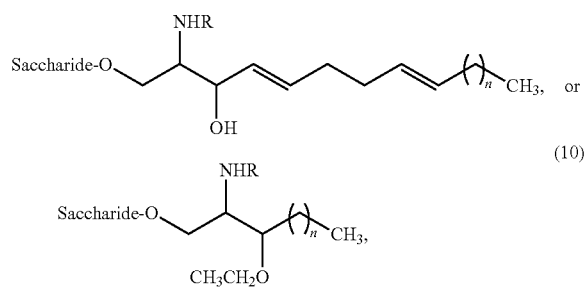

wherein n is an integer from 1 to 40, NHR is NH$_2$ or an amide of a saturated, unsaturated, or polyunsaturated (i.e., having at least two double bonds in the fatty acid chain) fatty acid having from 0 to 40 carbons in the chain. In some embodiments, n is an integer selected from the group consisting of 1, 2, 3, 4, 5, 6, 7, 8, 9, 10, 11, 12, 13, 14, 15, 16 or 17; More particularly, in some embodiments, n can be 7, 10, 11, 13 or 14. In some embodiments, the fatty acid is unsubstituted or alpha-hydroxylated. In other embodiments the long chain fatty acid is substituted. In other embodiments still, the R fatty acid member has from 14 to 28 carbon atoms in the fatty acid chain. In some embodiments, the long chain fatty acid is an unsubstituted or an alpha-hydroxylated C16, C18, C20, C22, or C24 fatty acid. In some embodiments, the fatty acid is an unsubstituted omega-3 or omega-6 or omega 9 fatty acid which may be optionally substituted with an alpha-hydroxyl group. In some further embodiments of such, the fatty acid is a C16, C18, or C18 fatty acid. In some embodiments, the compound comprises a 4,8-sphingadiene backbone. In some further embodiments of any of the above, the long chain fatty acid is a polyunsaturated fatty acid. In some embodiments of the above, the long chain fatty acid is an α-hydroxy fatty acid (e.g., a substituted or unsubstituted α-hydroxy palmitic acid or stearic acid) joined at the amide bond to a sphingoid base. In other embodiments of any of the above, R' is the saccharide moiety of a glycosphingolipid selected from GA2, GA1, GM1b, GD1c, GD1α, GM3, GM2, GM4, GM1a, GD1a, GT1a, GT1α, GD3, GD2, GD1b, GT1b, GQ1b, GQ1bα, GT3, GT2, GT1c, GQ1c, GP1c, Gb3, Gb4, sailyl-paragloboside, globoside, sulfatide and GP1cα. Accordingly, the saccharide moiety can be a mono-, di-, tri-, tetra-, penta-, hexa-, hepta-, octa-, nano-, or deca-saccharide. In some embodiments, the saccharide moiety can be the moiety of GM3, GM2, GM1a, GD1a, GT1a, or GT1α. In exemplary embodiments, the compound of formula (1)-(10) has the stereoisomerism of a corresponding naturally occurring glycolipids. In some embodiments, wherein the glycolipid has one or more double bond, the double-bond may be independently cis or trans, or a mixture thereof. In some embodiments, the double bonds are in the trans configuration.

In yet other embodiments, the compounds according to the invention, include the compounds of formulae (1), (2), (3), (4), (5), (6), (7), (8), (9) or (10) comprise an omega-3 fatty acid (e.g., DHA (docahexaenoic acid), EPA (eiocosapentaenoic acid)) or an omega-6 fatty acid (e.g., GLA (gamma linolenic acid)) as the polyunsaturated fatty acid. In a further embodiment of such compounds, n is 7, 10, 11, 12, 13 or 14. In a still further embodiment, the saccharide moiety can be the oligosaccharide moiety of GM3, GM2, GM1a, GD1a, GT1a, sialyl-paragloboside or GT1α.

In another embodiment of the compounds of formulae (1), (2), (3), (4), (5), (6), (7), (8), (9) or (10), the polyunsaturated fatty acid has non-conjugated double bonds. In a further embodiment of such, the polyunsaturated fatty acid is arachidonic acid. In yet other embodiments, the polyunsaturated fatty acid has 2, 3, 4, 5, or 6 non-conjugated double bonds; or at least two, three, four, or five non-conjugated double bonds. In still further embodiments, n is 7, 10, 11, 12, 13 or 14.

In another embodiment of compounds of formulae (1)-(10), the saccharide moiety, is selected from the glycans of the glycolipid families of Gala (Ga) (e.g., galactosyl-ceramides, sulfatides, sulfated digalactosides), Gluco, Globo (Gb), Isoglobo (iGb), Lacto (Lc), Neolacto (nLc), Ganglio (Gg), Isoganglio (iGg), Lactoganglio (LcGg) and Gangliosides (for example the a-, b- and c-series). In a further set of such embodiments, the fatty acid is palmitic, stearic or oleic acids.

In another embodiment of compounds of formula (1)-(10), the saccharide moiety, is selected from the group consisting of
Neu5Acα3Galβ4Glc—;
GalNAcβ4(Neu5Acα3)Galβ4Glc—;
Galβ3GalNAcβ4(Neu5Acα3)Galβ4Glc—;
Neu5Acα3Galβ3GalNAcβ4(Neu5Acα3)Galβ4Glc—; and
Neu5Acα8Neu5 Acα3Galβ3GalNAcβ4(Neu5Acα3) Galβ4Glc—.

In a further set of such embodiments, the fatty acid is DHA, EPA, or GLA.

In another aspect, the invention provides pharmaceutical compositions for treating a disorder selected from cancer, malignancy, hyperinsulinemia, hypoglycemia and hyperinsulinemia with hypoglycemia, a neurological disorder (e.g., Huntington's Disease, GM3 synthase deficiency, GM2 synthase deficiency, Parkinson's Disease, multiple systems atrophy, atypical Parkinson's Disease, a tauopathy) comprising a compound of the invention and a pharmaceutically acceptable excipient. In another embodiment, the pharmaceutical compositions are in unit dose format and each unit dose provides a therapeutically effective amount of one or more compounds for use according to the invention. The compositions, are formulated for oral, intraperitoneal, intranasal, topical, transcutaneous, subcutaneous, or intravenous administration.

In some embodiments, the above compositions can comprise a plurality of glycolipid analogs wherein each has a saccharide moiety of a different glycolipid. In some such embodiments, the administered glycosphingolipid consist of at least two or three such glycosphingolipids. In still other embodiments, the administered glycosphingolipid consist of at least 80%, 90%, 95%, or 98% of a single glycosphingolipid having a saccharide moiety of a naturally occurring mammalian glycosphingolipid.

In yet another aspect, the invention provides methods for treating a disease by administering a therapeutically effective amount of a glycolipid. This method optionally includes the administration of a therapeutically effective amound of at least a second therapeutic agent to a subject in need thereof. Exemplary glycolipids include, for example, those of the present invention and a those disclosed and/or claimed in any of U.S. patent application Ser. Nos. 10/485,195; 10/485,892; 10/487,841; 60/452,796; 11/666,577; 60/626, 678; and 10/547,566 which are each incorporated herein by reference particularly with respect to such compound subject matter Exemplary indications for this treatment include malignancies that are resistant or unresponsive to one or more antibodies or tyrosine kinase inhibitors, hematologic and solid tumors, congenital and non-congenital hyperinsulinemia, hypoglycemia, hyperinsulinemia with hypoglycemia, Parkinson's disease, Huntington's disease, mutliple systems atrophy, GM3 synthase deficiency, GM2 synthase deficiency, Parkinson's Disease, multiple systems atrophy, atypical Parkinson's Disease, and a tauopathy.

In another embodiment, the present invention provides a method of treating or inhibiting development of a post-prandial hypoglycemia, fasting hypoglycemia, neonatal hypoglycemia, hypoglycemia secondary to dialysis. The method includes the step of administering to the subject a therapeutically effective amount of a glycolipid. The postprandial hypoglycemia treated or inhibited by methods and compositions of the present invention is, in another embodiment, associated with a Nissen fundoplication or gastric-bypass surgery In another embodiment, administration of a therapeutically effective amount of a glycolipid to a subject suppresses insulin secretion by the subject.

Methods of the invention can be used for treating different cancers, both solid tumors and soft-tissue tumors alike. Non-limiting examples of cancers amendable to the treatment of the invention include breast cancer, colorectal cancer, rectal cancer, non-small cell lung cancer (NSCLC), non-Hodgkins lymphoma (NHL), renal cell cancer, prostate cancer, liver cancer, pancreatic cancer, soft-tissue sarcoma, Kaposi's sarcoma, sarcoma, renal cell carcinoma, carcinoid carcinoma, head and neck cancer, glioblastoma, melanoma, ovarian cancer, gastric cancer, mesothelioma, and multiple myeloma. In certain aspects, the cancers are metastatic. In other aspects, the cancers are non-metastatic.

In another embodiment, a compound of the invention utilized in methods and compositions of the present invention exhibits an improvement in a desirable biological property relative to the natural glycolipid. In another embodiment, the biological property is improved biological half-life. In another embodiment, the biological property is improved affinity for the insulin receptor. In another embodiment, the biological property is improved potency for antagonism of the insulin receptor. In another embodiment, the biological property is any other desirable biological property known in the art. Each possibility represents a separate embodiment of the present invention.

BRIEF DESCRIPTION OF THE DRAWINGS

FIG. 6A—Lyso-GM3 and Sphingosine; FIG. 6B—Triton X-100 and Sphingosine; FIG. 6C—Reaction-low enzyme concentration; and FIG. 6D—Reaction-high enzyme concentration.

DETAILED DESCRIPTION

Figure 1:
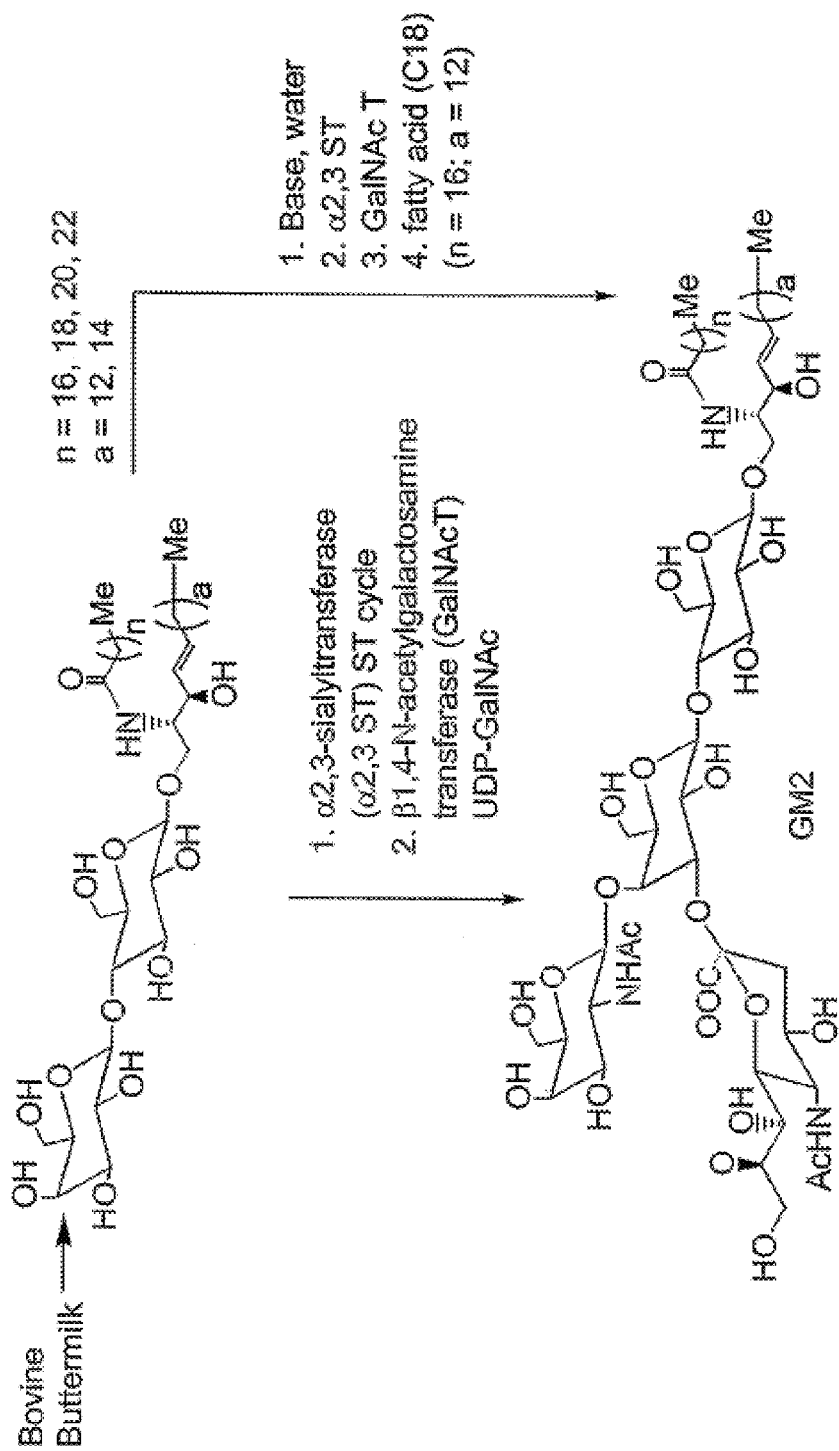
FIG. 1 is a schematic diagram of two methods for synthesis of the ganglioside GM2 by enzymatic synthesis using as the starting material lactosylceramide obtained from bovine buttermilk.
Figure 2:
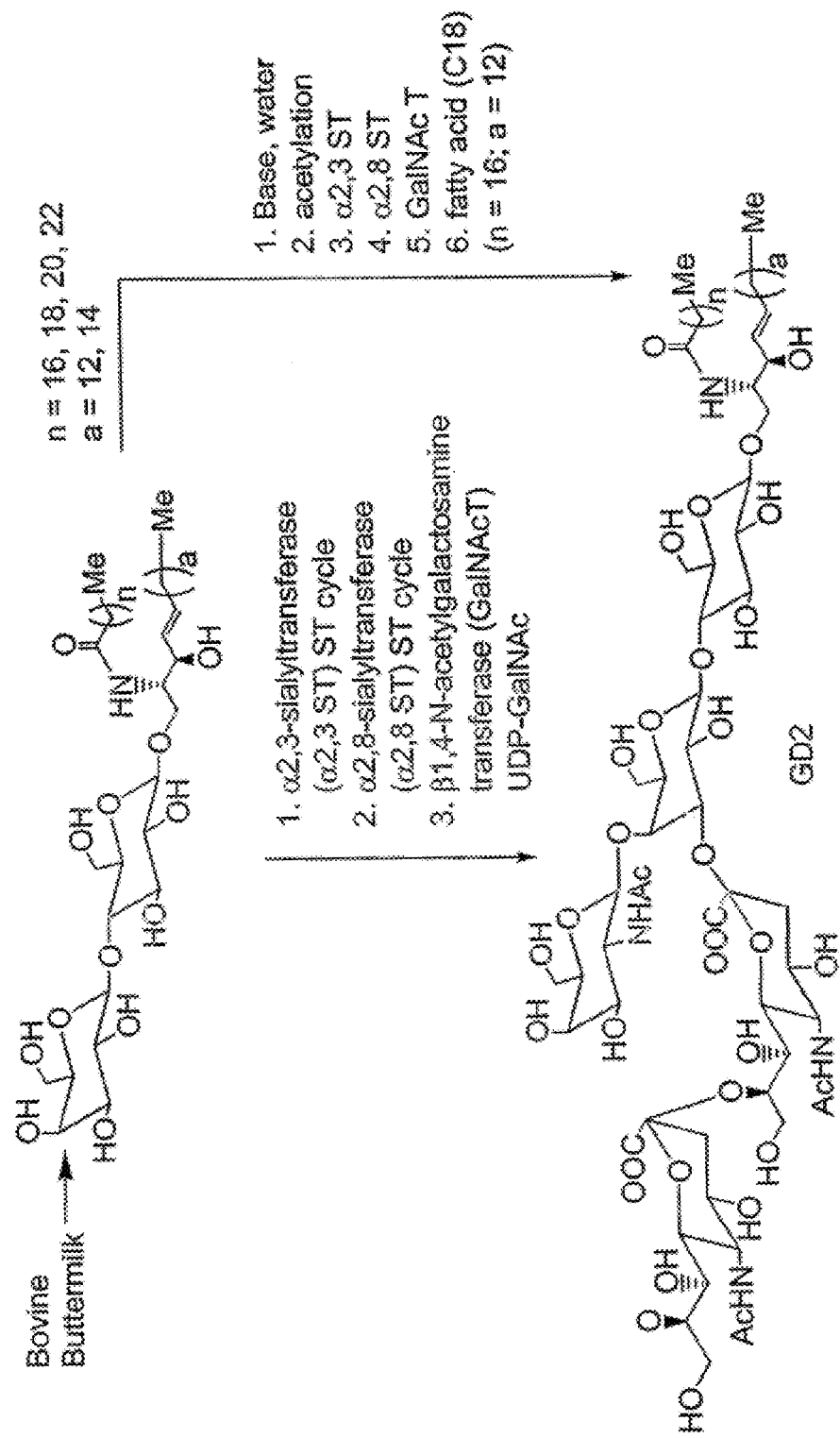
FIG. 2 is a schematic diagram of two methods for synthesizing the ganglioside GD2 from lactosylceramide obtained from bovine buttermilk.
Figure 3:
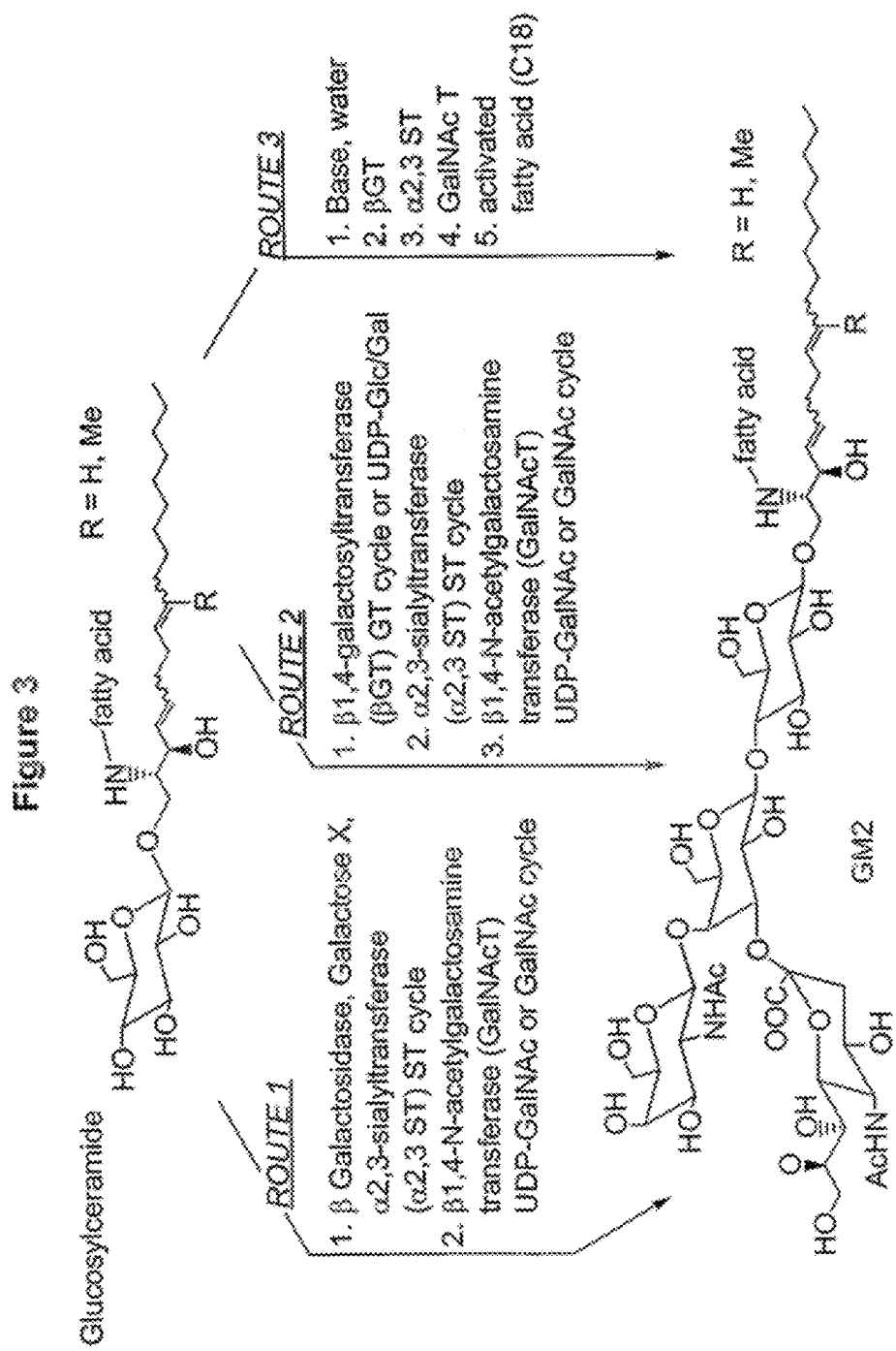
FIG. 3 is a collection of three routes for synthesizing a GM2 ganglioside using a plant glucosylceramide as the starting material.
Figure 4:
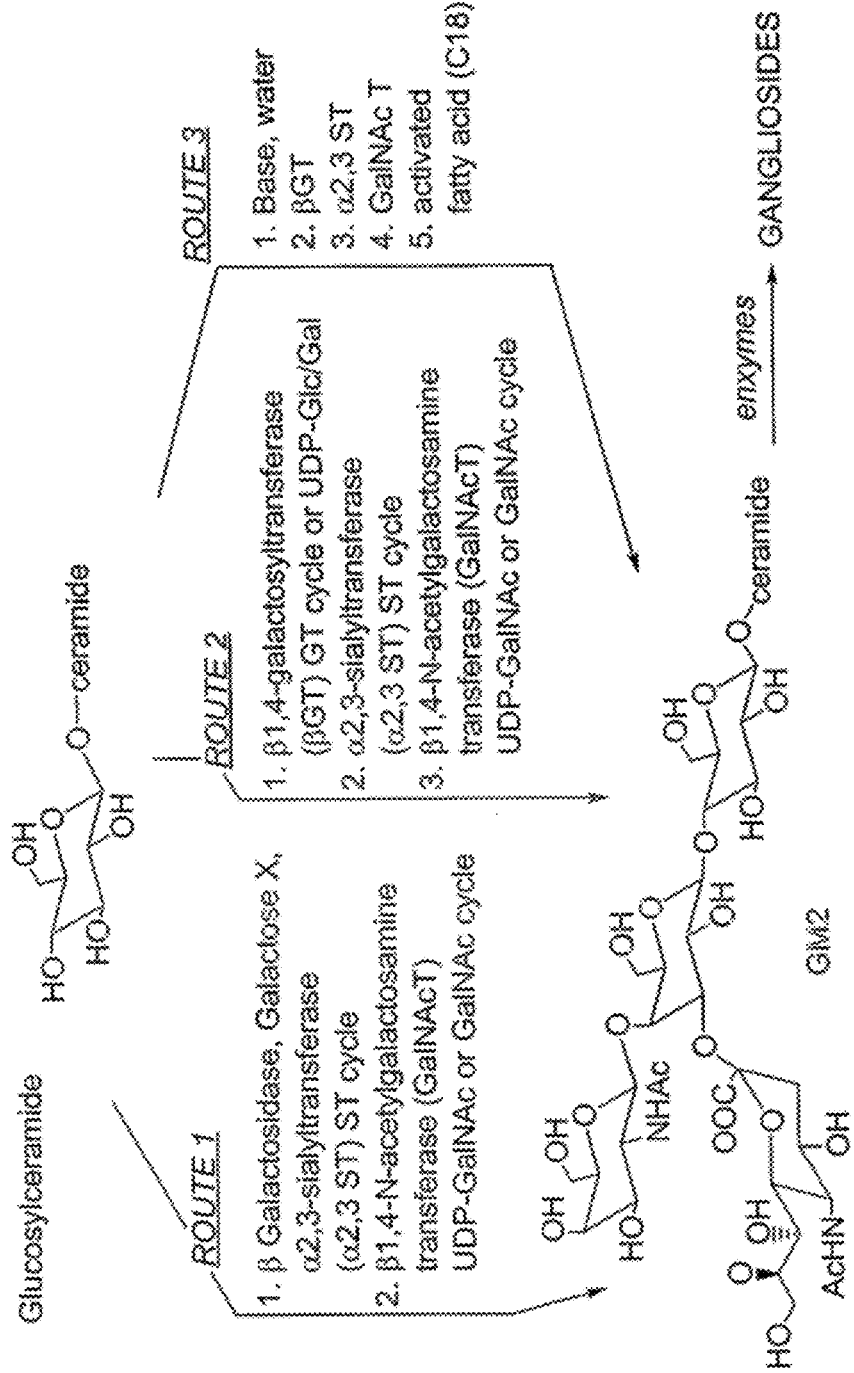
FIG. 4 is a collection of three routes for synthesizing GM2 and other gangliosides starting from a glucosylceramide.
Figure 5:
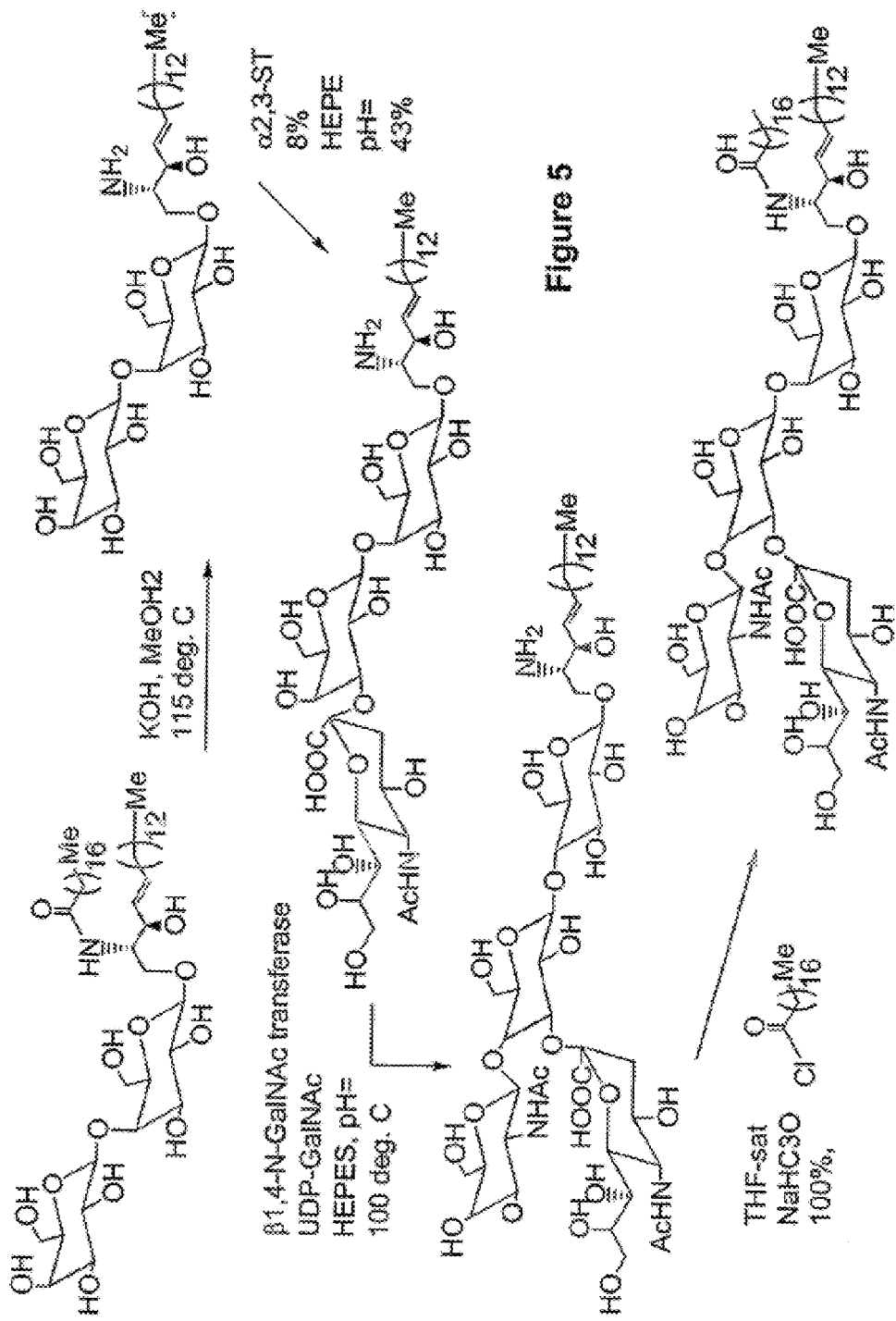
FIG. 5 is a scheme used for synthesis of the ganglioside GM2 from lactosylceramide via deacylation, two consecutive enzymatic glycosylations, and final chemical acylation.
Figure 6:
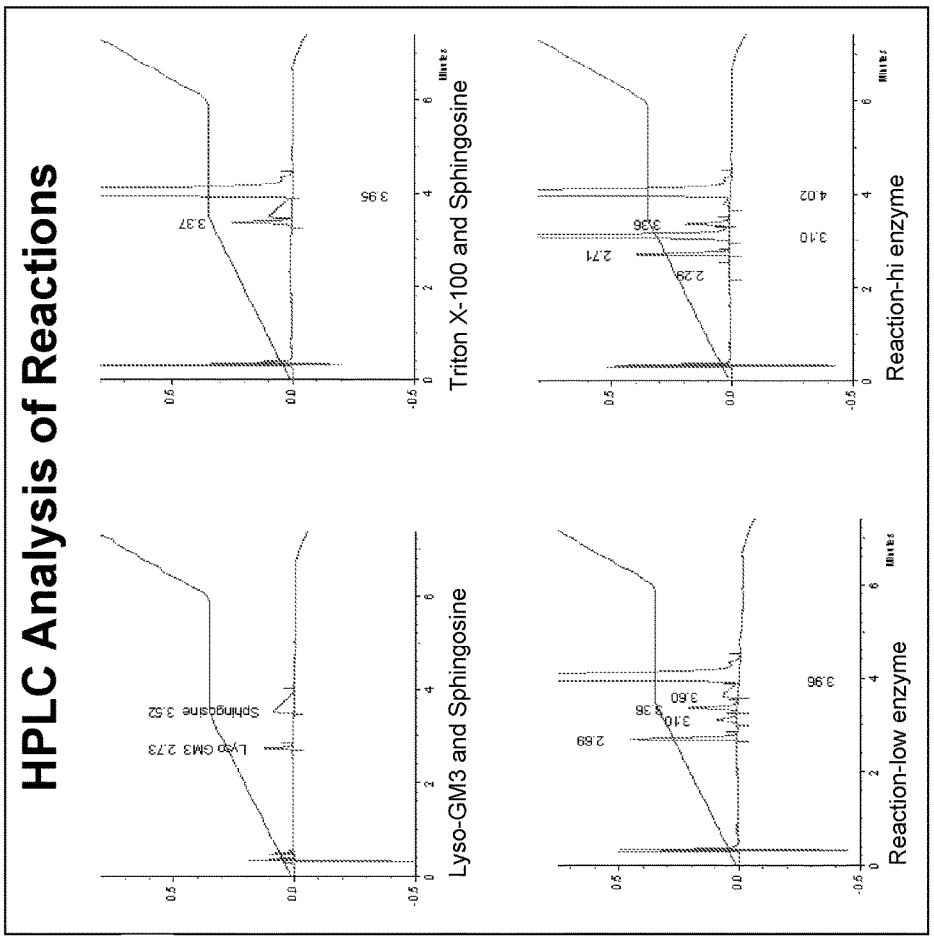
FIG. 6A-FIG. 6D. HPLC monitoring of an endoglycanase reaction(s). Transfer of the fluorinated GM1 sugar donor was monitored using an HPLC reverse phase method on a Chromolith RP-8e column with eluants of 0.1% trifluoroacetic acid (TFA) in acetonitrile (ACN) to 0.1% TFA in $H_2O$. Exemplified results of HPLC monitoring of a glycosynthase reaction for a *Rhodococcus* E351S mutant is depicted.
Figure 7:
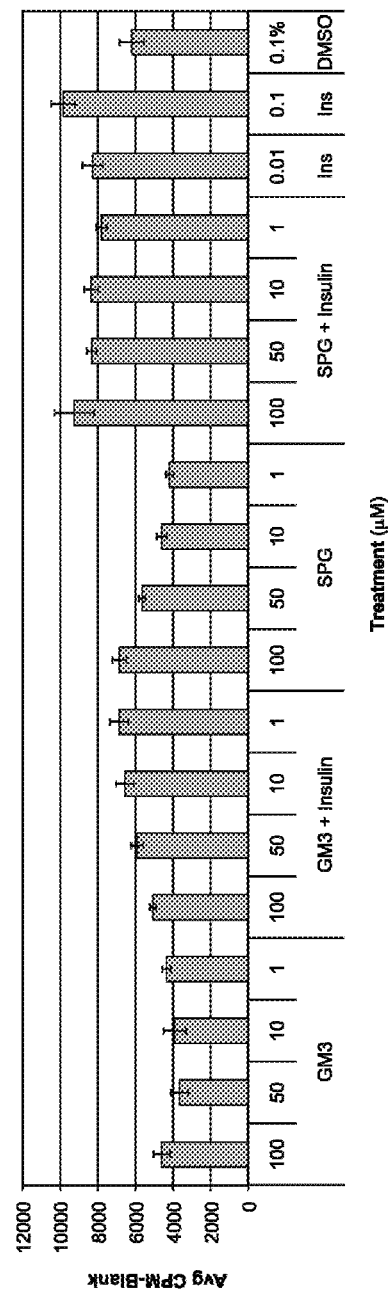
FIG. 7. Effect of glycolipids, GM3 and α-2,3-sialylparaglobside (SPG), on glucose uptake upon insulin stimulation of primary human adipocytes.

The present invention provides novel glycolipid compositions and methods of using these compositions to treat a congenital or non-congenital disorder, such as a disease characterized by a ganglioside deficiency. Exemplary disorders include cancer, atypical Parkinson's disease; Huntington's disease, multiple systems atrophy, GM3 synthase deficiency, GM2 synthase deficiency, hyperinsulinemia, hypoglycemia, hyperinsulinemia with hypoglycemis, a tauopathy, or another neurological disorder or condition associated with an increased aggregation of tau protein. The method includes administering to a subject in need thereof of a composition of the invention in a therapeutically effective amount.

Exemplary compounds of the invention have improved structures over lyso-GM1, GM1(stearate) and GM3 (stearate) when injected or given orally. These structures exhibit improved biodistribution, (e.g., brain delivery), improved pharmacokinetics, and improved oral bioavailability.

In some embodiments, the compound of Formula (1) to (10) has a saccharide moiety selected from those set forth in the following table of gangliosides:

| | |
|---|---|
| Neu5Ac3Gal4GlcCer | GM3 |
| GalNAc4(Neu5Ac3)Gal4GlcCer | GM2 |
| Gal3GalNAc4(Neu5Ac3)Gal4GlcCer | GM1a |
| Neu5Ac3Gal3GalNAc4Gal4GlcCer | GM1b |
| Neu5Ac8Neu5Ac3Gal4GlcCer | GD3 |
| GalNAc4(Neu5Ac8Neu5Ac3)Gal4GlcCer | GD2 |
| Neu5Ac3Gal3GalNAc4(Neu5Ac3)Gal4GlcCer | GD1a |
| Neu5Ac3Gal3(Neu5Ac6)GalNAc4Gal4GlcCer | GD1α |
| Gal3GalNAc4(Neu5Ac8Neu5Ac3)Gal4GlcCer | GD1b |
| Neu5Ac8Neu5Ac3Gal3GalNAc4(Neu5Ac3)Gal4GlcCer | GT1a |
| Neu5Ac3Gal3GalNAc4(Neu5Ac8Neu5Ac3)Gal4GlcCer | GT1b |
| Gal3GalNAc4(Neu5Ac8Neu5Ac8Neu5Ac3)Gal4GlcCer | GT1c |
| Neu5Ac8Neu5Ac3Gal3GalNAc4(Neu5Ac8Neu5c3)Gal4GlcCer | GQ1b |

Additionally the invention provides for the use of other glycolipids in treating a disorder selected from cancer, atypical Parkinson's disease; Huntington's disease, multiple systems atrophy, GM3 synthase deficiency, GM2 synthase deficiency, a tauopathy, or another neurological disorder or condition associated with an increased aggregation of tau protein including, for instance, the glycolipids of disclosed herein. These compounds to be administered to treat a disorder (e.g., cancer, atypical Parkinson's disease; Huntington's disease, multiple systems atrophy, GM3 synthase deficiency, GM2 synthase deficiency, a tauopathy, or another neurological disorder or condition associated with an increased aggregation of tau protein) include compounds according to the formula:

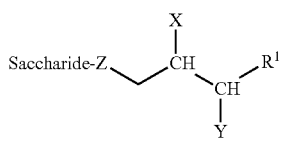

wherein Z, X, Y and $R^1$ have their identities disclosed herein including in those references incorporated herein by reference (e.g., U.S. Patent Application Publication No. 2007-0275908; U.S. Patent Application Publication No. US 2005/0239741; U.S. Patent Application Publication No. US 2005/0245735; and U.S. Patent Application Publication No. US 2005/0032742).

These compounds also include the neutral glycosphingolipids and neutral glycosyl sphingosines disclosed U.S. Patent Application Publication No. US 2005/0245735 which is incorporated by reference in its entirety.

These compounds also include sialylated oligosaccharide glycolipids disclosed in U.S. Patent Application Publication No. US 2005/0032742 which is incorporated herein by reference. In some embodiments, the oligosaccharide is a glycosylated ganglioside, ceramide, or sphingosine or an analogue of same.

Other compounds of use according to the invention include those disclosed in commonly owned U.S. Patent Application Publication Nos. US 2005/0245735; US 2005-0032742; US 2005-0239741; US 2007-0275908; and US 2008-0125392, each of which is incorporated by reference therein in its entirety for all purposes.

In exemplary embodiments, a compound of Formula (1), (2), (3), (4), (5), (6), (7), (8), (9) or (10) associates with the insulin receptor inhibiting cellular signalling. In a more preferred embodiment, the glycolipid inhibits the upregulation and transport of Glut-4 or Glut-2 to the cell surface. In another embodiment, the glycolipid reduces glucose uptake by the cell. In another exemplary embodiment, the saccharide of Formula (1), (2), (3), (4), (5), (6), (7), (8), (9) or (10) is a sugar of GM3, sialylparagloboside. Further, administration of compounds from Formula (1), (2), (3), (4), (5), (6), (7), (8), (9) or (10) based on the glycan structures of sialylparagloboside, GD1a or GM3 to a subject with hypoinsulinemia, hypoglycemia or hypoinsulinemia with hypoglycemia will reduce the hypoglycemic state, decrease insulin secretion, or reduce the morbidities and mortalities associated with the disease state of the subject.

In some embodiments, the compound selected from Formula (1), (2), (3), (4), (5), (6), (7), (8), (9) or (10) is administered to a subject or patient to replace a missing or low level glycolipid in the subject. For example, type II diabetes is associated with reduced levels of sulfatide (Buschard, Diabetes, 55: 2826-2834 (2006)). Supplementation of sulfatide (e.g., ceramide fatty acid of C16:0) inhibited glucose stimulation of insulin secretion by activation of the $K_{ATP}$ channels, in vitro. In addition, the exogenous sulfatide increased the expression of adiponectin while reducing inflammatory responses by decreasing the levels of TNF-alpha, IL-6 and IL-8 in human adippose tissue, in vitro (Bruun, Mol Cell Endocrinol, 263: 142-148 (2007)). In a preferred embodiment, a compound selected from Formula (1), (2), (3), (4), (5), (6), (7), (8), (9) or (10) will reduce insulin secretion from congenital or noncongenital diseases. In a more preferred embodiment, the congenital disease is Congenital Hyperinsulinemia (e.g., Familial Hyperinsulinemia). In an even more preferred embodiment, a compound from Formula (1), (2), (3), (4), (5), (6), (7), (8), (9) or (10) contains the saccharide moiety of sulfatide or GM4.

In another aspect, the invention provides methods of treating cancer, atypical Parkinson's disease; Huntington's disease, multiple systems atrophy, GM3 synthase deficiency, GM2 synthase deficiency, a tauopathy, or another neurological disorder or condition associated with an increased aggregation of tau protein a subject by administering to the subject one or more of the compounds selected from formula (1) to (10) in which the compound has a saccharide moiety of a deficient ganglioside or of a ganglioside which is downstream of a deficient ganglioside in the subject. In some embodiments, the ganglioside deficiency state may be mediated, exacerbated or caused by the condition or disease to be treated or by a reduced level of activity or absence of any of the enzymes involved in mammalian ganglioside synthesis or anabolism (e.g., ceramide glycosyl transferases, galactosyltransferases, sialyltransferases, and GalNAc transferases).

In certain aspects, the present invention provides a method for treating hyperinsulinemia, by administering effective amounts of compounds from Formula (1), (2), (3), (4), (5), (6), (7), (8), (9) or (10) and combining this treatment with the administration of drugs that reduce insulin or insulin like growth factor (e.g., IGF-1 and IGF-2) secretion, drugs and methods for increasing glucose levels, diet, diuretic, chemotherapy, radiation and surgery.

In an exemplary embodiment, the treatment uses a compound of Formula (1), (2), (3), (4), (5), (6), (7), (8), (9) or (10) in combination with one or more of additional treatment methods including sulfonylureas (e.g., diazoxide), somatostatin analogs (e.g., Octreotide®), calcium channel blockers (e.g., nifedipine), glucagon, IGF-1, insulin, glucocorticoids, growth hormone, glucagon like peptides (e.g., GLP-1, exendin-4, exendin peptide derivatives, exendin peptide antagonists and extended formulations thereof), glucose (e.g., IV, oral or gastrostomy), pancreatectomies, and tumor resection.

In some embodiments the glycolipid is capable of inhibiting cell proliferation, initiating apoptosis or is capable of killing the malignant cells independent of any additional antineoplastic therapies including antibodies. For example, GM3 can be used to treat certain CNS malignancies including glioma and bladder cancer (PCT Patent Application Serial No. WO9852577; Fujimoto, J Neuro-Oncology, 71: 99-106 (2005); Watanabe, Cancer Res, 62: 3850-3854 (2002), 9-O-acetyl-GD1b can treat CNS malignancies and breast cancer (Abad-Rodriguez, J Neurochemistry, 74: 2547-2556 (2006), sialyl-paragloboside can inhibit leukemias and Burkitt lymphoma (Schaade, Med Microbiol Immunol, 188: 23-29 (1999) and GD1b, GT1b and GQ1b suppress the growth of melanoma (Kanda, J Invest Dermatol, 117: 284-293 (2001)).

In certain aspects, the present invention provides a method for treating cancer, by administering effective amounts of compounds from Formula (1) to (10) combined with one or more antibodies directed against the tumor or tumor environment and combining this treatment with the administration of radiation treatment or chemotherapeutic agents to a patient susceptible to, or diagnosed with cancer. A variety of chemotherapeutic agents may be used in the combined treatment methods of the invention.

In one embodiment, the present invention can be used for increasing the duration of survival of a human patient susceptible to or diagnosed with a cancer, increasing progression free survival of a human patient susceptible to or diagnosed with a cancer, increasing response rate in a group of human patients susceptible to or diagnosed with a cancer, increases the duration of response in a subject with cancer, or to treat the signs and symptoms, ameliorate, or slow the progression of the malignancy when administered with an antibody directed towards an antigen or tyrosine kinase inhibitor. In an even more preferred embodiment, the response of the malignancy to the combination of agents is synergistic.

As will be understood by those of ordinary skill in the art, the appropriate doses of therapeutic and chemotherapeutic agents will be generally around those already employed in clinical therapies wherein the therapeutics are administered alone or in combination with other therapeutics. Variation in dosage will likely occur depending on the condition being treated. The physician administering treatment will be able to determine the appropriate dose for the individual subject.

DEFINITIONS

In accordance with the invention and as used herein, the following terms are defined with the following meanings, unless explicitly stated otherwise.

The terms "cancer", "cancerous", "malignancy" and "malignant: refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, Hodgkin's disease, non-Hodgkins lymphoma, anaplastic large T-cell lymphoma, acute myelogenous leukemia (AML), chronic lympocytic leukemia (CLL), cutaneous T-cell lymphoma, follicular lymphoma, Burkitt's lymphoma, peripheral T-cell lympoma, brain, as well as head and neck cancer, and associated metastases. Examples of head and neck cancers include, but are not limited to, adenoid cystic carcinomas localized, for example to the tongue, parotid gland, nose, palate, skin, neck, submandibular gland, glottis, sinus, epiglottis, buccal space, nerves, larynx, mouth, pharynx, or cheek.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

Atypical Parkisonian diseases or syndromes refers to a group of disorders whose clinical features overlap those of idiopathic Parkinson's disease. The four major Parkinsonian syndromes embrace three important neurodegenerations, multiple system atrophy, progressive supranuclear palsy, and corticobasal degeneration, and a lacunar cerebrovascular disorder, vascular parkinsonism (see, Gilman S., Clin. Geriatr. Med 22:827-42 (2006). In embodiments, the conditions to be treated according to the invention can be any one of these four major syndromes.

The term "congenital disease" as used herein refers to a disease or disorder that is inherited genetically. The term is intended to include familial hyperinsulinemia (OMIM no. 256450, 601820, 606762, 602485, 609968, 609975, 610021) (e.g., persistent hyperinsulinemic hypoglycemia of infancy, ABCC8-related hyperinsulinism, GCK-related hyperinsulinism, HADHSC-related hyperinsulinism, GLUD1-related hyperinsulinism, KCNJ11-related hyperinsulinism, insulin receptor-related hyperinsulinism, UCP2-related hyperinsulinism, exercise induced hyperinsulinism, diffuse hyperinsulinism), Beckwith-Wiedemann Syndrome, Congenital Disorders of Glycosylation (CDG)(e.g., CDG-Ia-n, CDG-IIa-h), type II diabetes, polycystic kidney disease, hypopituitarism, hyperinsulinism, glycogen storage disease (Type I and III), organic acidurias (e.g., maple syrup urine disease, 3-hydroxymethylglutaryl-CoA lysase deficiency, glutaric acidemia type I and II, 3-methylglutaconic aciduria type 1, mevalonic aciduria, alpha-methylacetoacetic aciduria, short-chain acyl-CoA dehydrogenase deficiency, 3-methylcrotonyl-CoA carboxylase I deficiency, long-chain acyl-CoA dehydrogenase deficiency, carnitine-acylcarnitine translocase deficiency, carnitine palmitoyl-transferase II deficiency, medium chain acyl-CoA dehydrogenase deficiency), phosphoenolpyruvate carboxykinase deficiency, disorders of fatty acid oxidation (e.g., 3-hydroxyacyl-CoA dehydrogenase deficiency, very long chain acyl-CoA dehydrogenase deficiency, trifunctional protein deficiency), familial leucine sensitive hypoglycemia, insulin secreting tumors, insulin like growth factor (e.g., IGF-1, IGF-2) secreting tumors, Addison's disease, reactive hypoglycemia and idiopathic postprandial syndrome, Doege-Potter syndrome, hyperinsulin hyperammonia syndrome, multiple endocrine neoplasia, neurofibromatosis type 1, adrenal insufficiency (e.g., adrenal hyperplasias including ACTH-independent macronodular adrenal hyperplasia), Simpson-Golabi-Behmel syndrome type 1, idiopathic ketotic hypoglycemia, and reactive hypoglycemia and idiopathic postprandial syndrome. The term is also intended to include GM3 synthase deficiency (OMIM no. 609056; Amish Infantile Epilepsy Syndrome) in which the sialyltransferase (ST3Gal5; SIAT9) that prepares GM3 in the ganglioside biosynthetic pathway has decreased or absent biosynthetic activity. The term also is intended to include GM2 synthase deficiency [GM3 (Hematoside) Sphingolipodystrophy] in which the GalNAc-transferase (B4Galnt1) that prepares GA2, GM2 and GD2 in the glycolipid biosynthetic pathway has decreased or absent biosynthetic activity. The term is also intended to include Huntington's Disease (OMIM no. 143100) which has a glycolipid deficient phenotype that results in a reduction in the amount of higher glycolipids (e.g., GM2, GM1, GD2, GD1a, GT1a, GT1b, GQ1b) (Neurobiol Dis, 27:265-277 (2007)).

The term "noncongenital disease" as used herein refers to a disease or disorder that is not inherited genetically. The term is intended to include type II diabetes, acquired adrenal insufficiency, premature birth, sepsis, acquired hypopituitarism, gastric dumping syndrome, insulin secreting tumors, insulin like growth factor (e.g., IGF-1, IGF-2) secreting tumors, immunopathologic hypoglycemia, bowel bypass surgery or resection, reactive hypoglycemia and idiopathic postprandial syndrome, acquired hypoglycemia resulting from dialysis, hypoglycemia resulting from organ (e.g., kidney, liver, heart, lung) transplantation, medication or toxin induced hypoglycemia, asphyxia, hypocalcemia, opoid withdrawal and Nissen fundoplication.

The compounds for use according to the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds (e.g., D, $^{13}$C, $^{18}$O) for use according to the present invention, whether radioactive or not, are intended to be encompassed within the scope of the present invention.

The term "substituted" as used herein means that a hydrogen atom has been replaced with another monovalent group (e.g., halo, haloalkyl, hydroxy, thiol, alkoxy, thiohaloalkyl, amino, and the like), or that two hydrogen atoms of the same atom have been replaced by a divalent group.

The terms "halo" or "halogen" as used herein refer to Cl, Br, F or I. The term "haloalkyl" and the like, refer to an alkyl group, as defined herein, wherein at least one hydrogen atom of the alkyl group is replaced by a Cl, Br, F or I. A mixture of different halo atoms may be used if more than one hydrogen atom is replaced. For example, a haloalkyl includes chloromethyl (—CH$_2$Cl) and trifluoromethyl (—CF$_3$) and the like.

The term "alkyl," by itself or as part of another substituent, means, unless otherwise stated, a straight or branched chain, or cyclic hydrocarbon radical, or combination thereof, which is saturated, and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

The term "alkylene" by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkyl," "alkenyl" and "alkynyl" are meant to include both substituted and unsubstituted forms of the indicated radical. The terms also include, but are not limited to, forms of the radicals having 3 or fewer or 6 or fewer carbon atoms. Preferred substituents for each type of radical are provided below.

Substituents for the alkyl, alkenyl, alkynyl radicals can be one or more of a variety of groups selected from, but not limited to: —OR$^a$, =O, =NR$^a$, =N—OR$^a$, —NR$^a$R$^b$, —SR$^a$, -halogen, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^c$—C(O)NR$^a$R$^a$, —NR$^b$C(O)$_2$R$^a$, —NR$^e$—C(NR$^a$R$^b$R$^c$)=NR$^d$, —NR$^d$—C(NR$^a$R$^b$)=NR$^c$, —S(O)R$^a$, —S(O)$_2$R$^a$, —S(O)$_2$NR$^a$R$^b$, —NR$^b$SO$_2$R$^a$, —CN and —NO$_2$ in a number ranging from zero to (2m'+1), where m' is the total number of carbon atoms in such radical. R$^a$, R$^b$, R$^c$, R$^d$ and R$^e$ each preferably independently refer to hydrogen or unsubstituted alkyl. When a compound of the invention includes more than one of any R$^a$, R$^b$, R$^c$, R$^d$ or R$^e$ group, each of those groups are independently selected as well. For example, if there are two or more R$^a$ groups in a formula, each of those are independently selected. When R$^a$ and R$^b$ are attached to the same nitrogen atom, they can optionally be combined with the nitrogen atom to form a 5-, 6-, or 7-membered ring. For example, —NR$^a$R$^b$ is meant to include, but not be limited to, 1-pyrrolidinyl and 4-morpholinyl. From the above discussion of substituents, one of skill in the art will understand that the term "alkyl" is meant to include, but not be limited to, groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferred substituents are lower alkyl, lower alkoxy, hydroxy, and halo. The term "lower" indicates C$_1$ to C$_6$ carbons in the chain. In some embodiments, the total number of substituents for the alkyl, alkenyl, or alkynyl radical are independently in a number which is 0, 1, 2, 3 or 4. In a further embodiment, these substituents are independently selected from the group consisting of lower alkyl, lower alkoxy, hydroxy, and halo.

In some embodiments, according to the invention, the compound of the invention has a saccharide moiety with the structure:

Neu5Ac3Gal4Glc-(as in GM3);
GalNAc4(Neu5Ac3)Gal4Glc-(as in GM2)
Gal3GalNAc4(Neu5Ac3)Gal4Glc(as in GM1a)
Neu5Ac3Gal3GalNAc4Gal4Glc(as in GM1b)
Neu5Ac8Neu5Ac3Gal4Glc(as in GD3)
GalNAc4(Neu5Ac8Neu5Ac3)Gal4Glc(as in GD2)
Neu5Ac3Gal3GalNAc4(Neu5Ac3)Gal4Glc(as in GD1a)
Neu5Ac3Gal3(Neu5Ac6)GalNAc4Gal4Glc(as in GD1α.
Gal3GalNAc4(Neu5Ac8Neu5Ac3)Gal4Glc(as in GD1b)
Neu5Ac8Neu5Ac3Gal3GalNAc4(Neu5Ac3)Gal4Glc(as in GT1a)
Neu5Ac3Gal3GalNAc4(Neu5Ac8Neu5Ac3)Gal4Glc(as in GT1b)
Gal3GalNAc4(Neu5Ac8Neu5Ac8Neu5Ac3)Gal4Glc(as in GT1c)
Neu5Ac8Neu5Ac3Gal3GalNAc4(Neu5Ac8Neu5c3)Gal4Glc(as in GQ1b)

See, Nomenclature of Glycolipids, IUPAC-IUB Joint Commission on Biochemical Nomenclature (Recommendations 1997); *Pure Appl. Chem.* 69: 2475-2487 (1997); *Eur. J. Biochem* 257: 293-298 (1998)) (www.chem.qmw.ac.uk/iupac/misc/glylp.html).

The term "sphingoid," as used herein, includes sphingosines, phytosphingosines, sphinganines, ceramides, and the like. Both naturally occurring and synthetically produced compounds are included. The naturally occurring sphingoid base has an alkyl chain length of from 14 to 22 carbons long, but is preferably 18 carbons long. Synthetic sphingoid bases can be longer or shorter (e.g., having from 2 to 40 carbons in the alkyl chain). A ceramide is an N-acetylated sphingoid base. The fatty acids of ceramides vary in chain lengths (14 to 40 carbons in the chain) and the presence or absence of a hydroxyl group at the α- or ω-carbon atom.

The term "glycosphingolipid" is a carbohydrate-containing derivative of a sphingoid or ceramide. The carbohydrate residue is attached by a glycosidic linkage to O-1 of the sphingoid or ceramide.

As used herein, the term "heteroatom" is meant to include oxygen (O), nitrogen (N), and sulfur (S).

Ganglioside analog refers to gangliosides in which the saccharyl moiety, the base (e.g., sphingoid-like backbone), or the fatty acid-derived hydrocarbon is of a structure other than that found in naturally occurring ganglioside. Unless indicated otherwise, the term ganglioside is meant to include ganglioside analogs as well as naturally occurring gangliosides.

The term "sialic acid" (abbreviated "Sia") refers to any member of a family of nine-carbon carboxylated sugars. The most common member of the sialic acid family is N-acetylneuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. Another sialic acid family member is 2-keto-3-deoxy-nonulosonic acid (KDN) (Nadano et al., *J. Biol. Chem.* 261: 11550-11557 (1986); Kanamori et al., *J. Biol. Chem.* 265: 21811-21819 (1990). Also included are 9-substituted sialic acids such as a 9-O—$C_1$—$C_6$ acyl-Neu5Ac like 9-O-lactyl-Neu5Ac or 9-O-acetylNeu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); Sialic Acids: Chemistry, Metabolism and Function, R. Schauer, Ed. (Springer-Verlag, New York (1992). The synthesis and use of sialic acid compounds in a sialylation procedure is described in, for example, International Patent Application Publication No. WO 92/16640, published Oct. 1, 1992.

In some embodiments, the compound of formula (1)-(10) is a glycolipid compound of a formula:

GM4

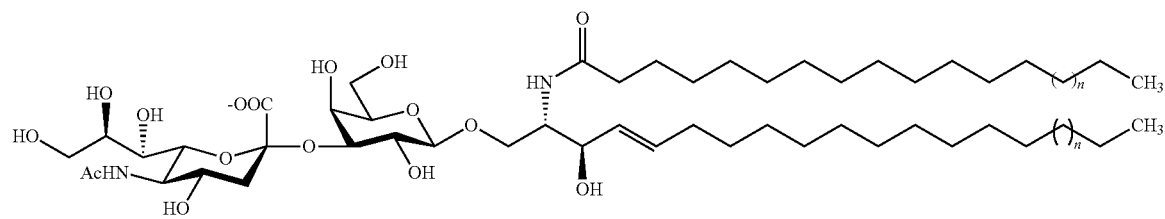

GM3

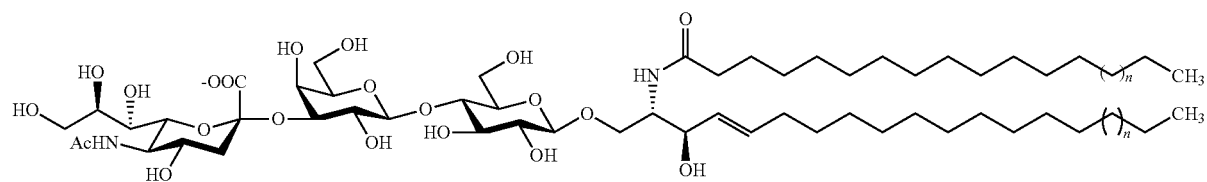

GD3

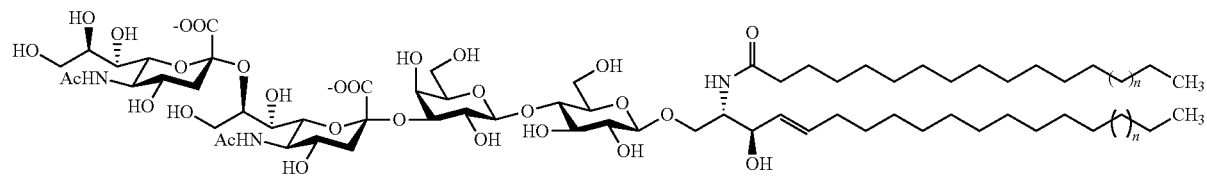

GM2

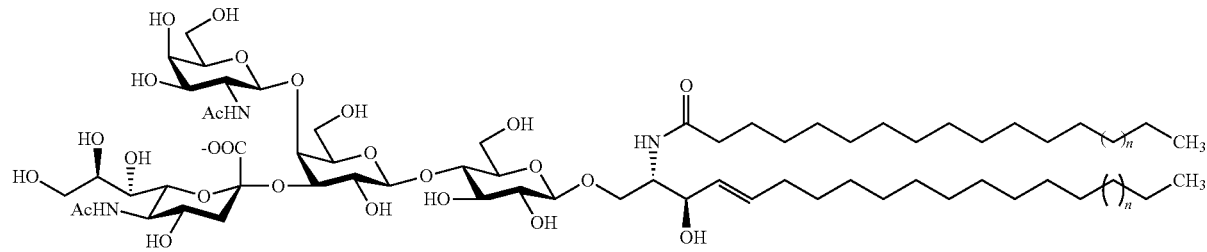

GM1

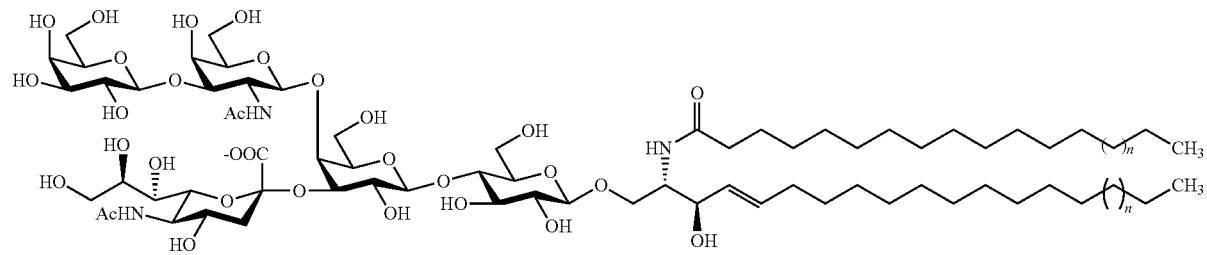

-continued
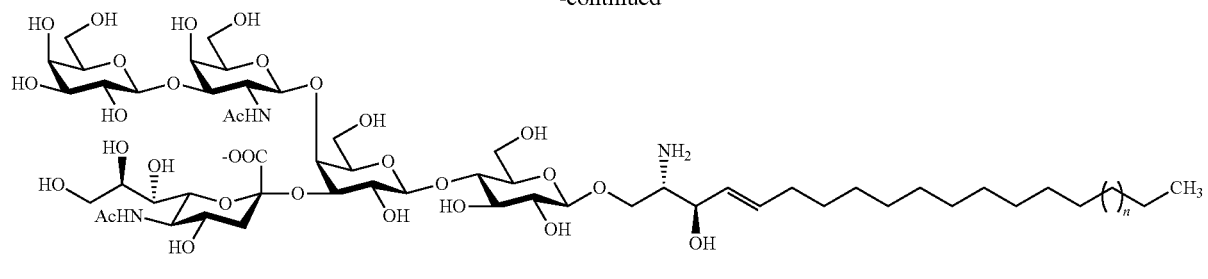
Lyso-GM1
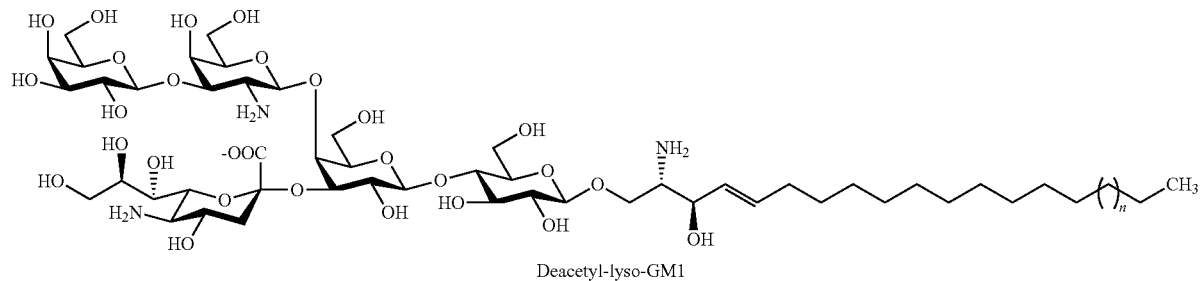
Deacetyl-lyso-GM1
GD1a
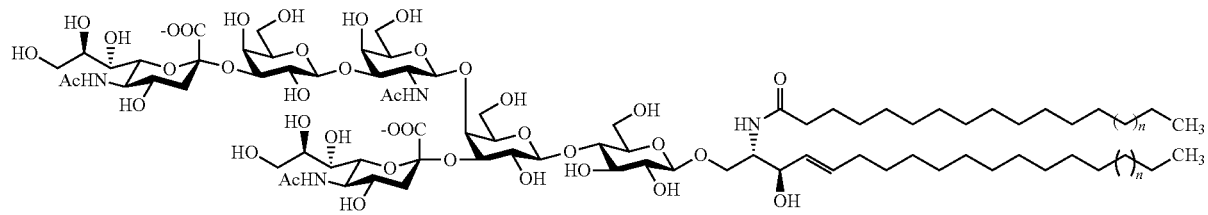
GD1b
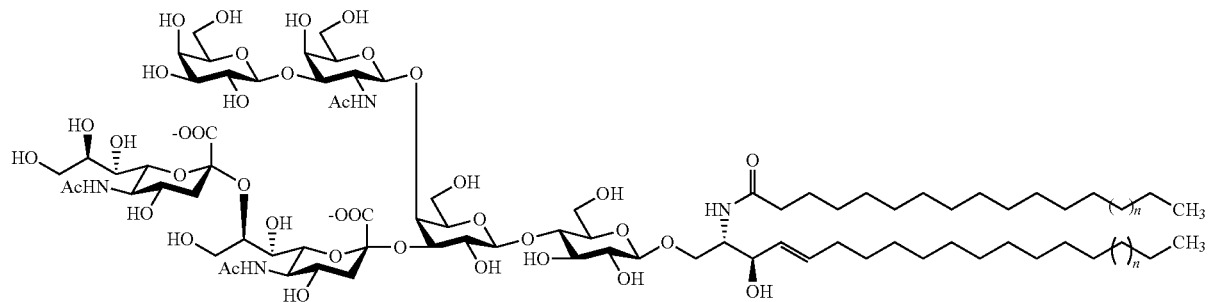
GT1a
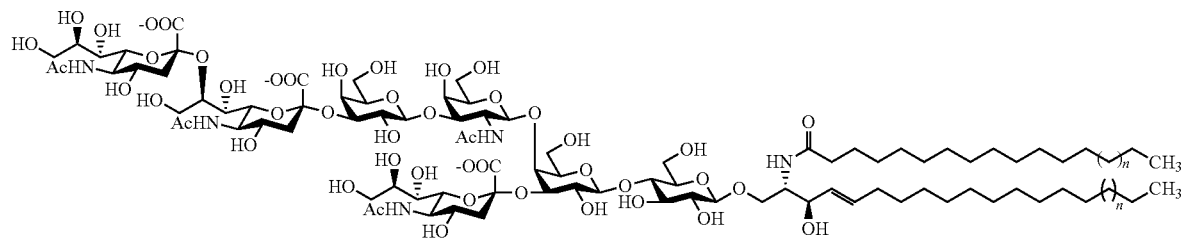

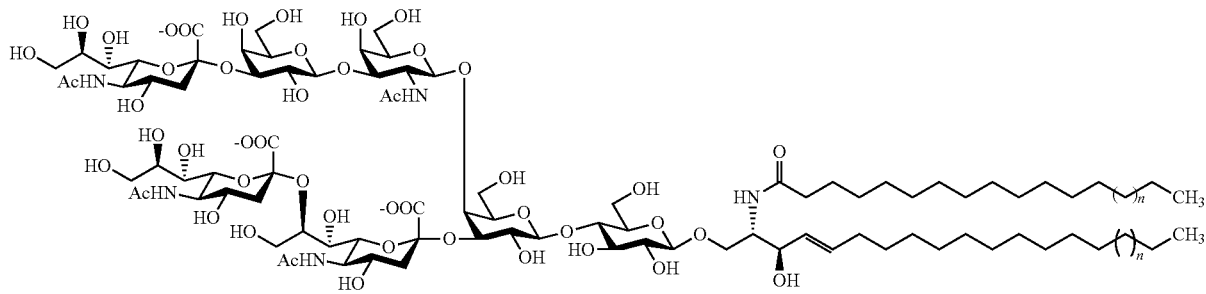

GT1b

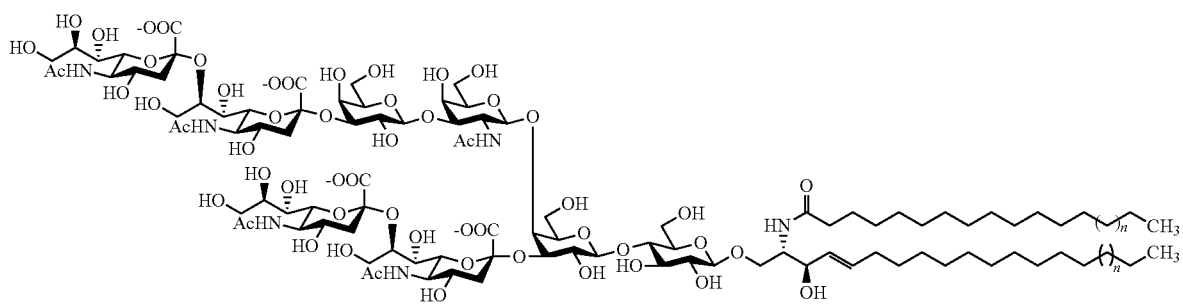

GQ1b in which each n is independently as set forth above. In some embodiments of the above, each n is 1.

The terms "deficiency" and "deficiency state" refer to a large relative reduction in the levels of the referenced ganglioside or enzyme or enzyme activity in tissues or samples from a subject. Such deficiency states may generally exist, for instance, when the levels of a subject glycolipid are zero or undetectable or less than two-thirds, one-half, one-fourth, one-tenth, one-twentieth, or one-one hundredth of the levels for the comparable well-matched control group with a similar malignancy.

The term "fatty acid" refers to an aliphatic monocarboxylic acid which may be substituted or unsubstituted and saturated or unsaturated and have from 1 to 40 carbon atoms. In some embodiments, the fatty acid is from 2 to 40 carbon atoms in length, including the carboxyl moiety carbon. In further embodiments, the fatty acid is 14 to 24 carbon atoms in length and is saturated or unsaturated. In other embodiments, the fatty acid is unsubstituted and from 14 to 24 carbons in length and is saturated or unsaturated. If unsaturated, the double bond may be in the cis or trans conformation, or be a mixture thereof. In some embodiments, the fatty acid is unsaturated with at least one of the double bonds is in the trans configuration. Unsaturated fatty acids may be polyunsaturated, for instance, having from 1, 2, 3, or 4 double bonds. Exemplary fatty acids are stearic acid and oleic acid as well as the omega-3, omega-6, and omega 9 fatty acids of from 14 to 24 carbons in length. In some embodiments, the fatty acid is optionally substituted with an α-hydroxy or an α-alkoxy group or an acylated α-hydroxy group (acetyl α-hydroxy) which acylated compound may function as a prodrug of a compound of formulae (1), (2), (3), (4), (5), (6), (7), (8), (9) or (10). The aliphatic moiety may be linear or branched. In preferred embodiments of any of the above, it is linear.

"Commercial scale" refers to gram scale production of a compound of formulae (1), (2), (3), (4), (5), (6), (7), (8), (9) or (10) in a single reaction. In preferred embodiments, commercial scale refers to production of greater than about 50, 75, 80, 90, 100, 125, 150, 175, or 200 grams of a compound of formula (1), (2), (3), (4), (5), (6), (7), (8), (9) or (10). In some embodiments, the methods of use and manufacture of the pharmaceutical compositions involve the use of such compounds produced on a commercial scale.

Method of Preparing the Compounds

The compounds of formula (1), (2), (3), (4), (5), (6), (7), (8), (9) or (10) can be made by any method available to one of ordinary skill in the art. The saccharide moiety of the compounds for use according to the invention can be prepared by any means known in the art including those methods described in U.S. Pat. Nos. 5,922,577; 6,284,493; and 6,331,418, each of which is incorporated by reference herein in its entirety. Additional particularly suitable methods for making compounds for use according to the invention are described in U.S. Patent Application Publication No. US 2009-0170155; U.S. Patent Application Publication No. US 2009-0170155; and U.S. Patent Application Publication No. US 2009-0170155; which are assigned to the same assignee as the instant application; and in U.S. Pat. Nos. 6,440,703 and 6,030,815; and PCT International Patent Application Publications Nos. WO2004/080960, WO2003/016469, WO2005/118798 and WO2004/080960. Each of these references is incorporated herein by reference particularly with respect to their teachings as to how to synthesize various glycolipids.

The compounds of the invention and of use in the methods of the invention can be prepared using, unless otherwise indicated, conventional methods and protocols in chemistry and enzymology known in the art. For example, compounds for use according to the invention may be prepared by chemical and enzymatic processes as outlined further below.

Additional suitable synthetic approaches are disclosed in WO 2004/080960 A2 which is incorporated by reference herein in its entirety.

If the acceptor is a ceramide, the enzymatic step is optionally preceded by hydrolysis of the fatty acid moiety from the ceramide. Methods of removing a fatty acid moiety from a glycosphingolipid are known to those of skill in the art. Standard carbohydrate and glycosphingolipid chemistry methodology can be employed, such as that described in, for example, Paulson et al., *Carbohydrate Res.* 137: 39-62 (1985); Beith-Halahmi et al., *Carbohydrate Res.* 5: 25-30 (1967); Alais and Veyrieries, *Carbohydrate Res.* 207: 11-31; (1990); Grudler and Schmidt, *Carbohydrate Res.* 135: 203-218 (1985); Ponpipom et al.; *Tetrahedron Lett.* 1717-1720 (1978); Murase et al., *Carbohydrate Res.* 188: 71-80 (1989); Kameyama et al. *Carbohydrate Res.* 193: c1-c5(1989); Hasegawa et al. *J. Carbohydrate Chem.* 10: 439-459(1991); Schwarzmann and Sandhoff, *Meth. Enzymol.* 138: 319-341 (1987); Guadino and Paulson, *J. Am. Chem. Soc.* 116: 1149-1150 (1994) (including supplemental material, which is also incorporated herein by reference). For example, the fatty acid moiety can be removed by base hydrolysis. Once the glycosylation reactions are completed, the same or a different fatty acid can be attached to the product of the glycosylation reactions.

Methods for coupling a fatty acid are generally known in the art and examples are discussed herein. The N-acyl group (NHR) of a compound selected from formulae (1) to (10) can be derived from a wide variety of polyunsaturated fatty acids (or corresponding activated derivative, e.g., active ester, acid halide, etc.). Acylation can be carried out in the conventional way, for example, by reacting the starting products with an acylating agent, particularly with a reactive functional derivative of the acid, whose residue is to be introduced.

The invention also provides metal or organic base salts of the glycosphingolipid compounds for use according to the present invention having free carboxy functions, and these also form part of the invention. Also forming part of the invention are acid addition salts of glycosphingolipid derivatives, which contain a basic function, such as a free amino function, for example, esters with aminoalcohols.

Another suitable method of synthesizing a glycolipid of formula (1), (2), (3), (4), (5), (6), (7), (8), (9) or (10) can use wild type or mutant endoglycoceramidase as taught in WO/2005/118798 which is incorporated herein by reference in its entirety with respect to the methods of synthesis and enzymes used therein.

Further modifications can be made to the glycolipids synthesized using the endoglycoceramide synthase of the present invention. Exemplary methods of further elaborating glycolipids produced using the present invention are set forth in WO 03/017949; PCT/US02/24574; US2004063911 (although each is broadly directed to modification of peptides with glycosyl moieties, the methods disclosed therein are equally applicable to the glycolipids and method of producing them set forth herein). Moreover, the glycolipid compositions of the invention can be subjected to glycoconjugation as disclosed in WO 03/031464 and its progeny (although each is broadly directed to modification of peptides with glycosyl moieties, the methods disclosed therein are equally applicable to the glycolipids and method of producing them set forth herein).

The products produced by the above processes can be used without purification. However, for some applications it is desirable to purify the compounds. Standard, well-known techniques for purification of substrates are generally suitable. For example, thin or thick layer chromatography, column chromatography, ion exchange chromatography, or membrane filtration can be used. Moreover, membrane filtration, preferably utilizing a reverse osmotic membrane, or one or more column chromatographic techniques, can be utilized. For instance, membrane filtration wherein the membranes have molecular weight cutoff of about 3,000 to about 10,000 can be used to remove proteins such as glycosyl transferases. Nanofiltration or reverse osmosis can then be used to remove salts and/or purify the product saccharides (see, e.g., WO 98/15581).

Another exemplary purification strategy makes use of a membrane in conjunction with an organic solvent. Both glycolipids and glycosphingolipids can be purified by this method. Moreover, any of the intermediate enzyme reaction products described herein can be purified according to this method. The method includes concentrating a reaction product in a membrane purification system with the addition of an organic solvent.

Suitable solvents include, but are not limited to alcohols (e.g., methanol), halocarbons (e.g., chloroform), and mixtures of hydrocarbons and alcohols (e.g., xylenes/methanol). In a preferred embodiment, the solvent is methanol. The concentration step can concentrate the reaction product to any selected degree.

In yet another embodiment, the invention provides a pharmaceutical formulation comprising a glycolipid as set forth or incorporated by reference herein, e.g., of Formula (1), (2), (3), (4), (5), (6), (7), (8), (9) or (10), in admixture with a pharmaceutically acceptable carrier. The pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). For a brief review of methods for drug delivery, see, Langer, *Science* 249: 1527-1533 (1990).

The pharmaceutical compositions can be administered by a number of routes, for instance, the parenteral, subcutaneous, intravenous, intranasal, topical, oral or local routes of administration, such as by aerosol or transdermally, for prophylactic and/or therapeutic treatment. Commonly, the pharmaceutical compositions may be administered parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

The compositions containing the glycolipid compounds can be administered for prophylactic and/or therapeutic treatments. In therapeutic applications, compositions are administered to a subject already suffering from a disease, as described above, in an amount sufficient to cure or at least partially arrest the symptoms of the disease and its complications. Amounts effective for this use will depend, as discussed further below, on the particular compound, the severity of the disease and the weight and general state of the subject, as well as the route of administration, but generally range from about 0.5 mg to about 2,000 mg of substrate per day for a 70 kg subject, with dosages of from about 5 mg to about 200 mg of the compounds per day being more commonly used.

In prophylactic applications, compositions containing the compound for use according to the invention are administered to a subject susceptible to or otherwise at risk of a particular disease. Such an amount is defined to be a "prophylactically effective dose." In this use, the precise amounts again depend on the subject's state of health and weight, and the route of administration but generally range from about 0.5 mg to about 2,000 mg per 70 kilogram subject, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the substrates of this invention sufficient to effectively treat the subject.

Labeled substrates can be used to determine the locations at which the substrate becomes concentrated in the body due to interactions between the desired oligosaccharide determinant and the corresponding ligand. For this use, the compounds can be labeled with appropriate radioisotopes, for example, $^{125}I$, $^{14}C$, or tritium, or with other labels known to those of skill in the art.

The dosage ranges for the administration of the compounds for use according to the invention are those large enough to produce the desired effect. Generally, the dosage will vary with the age, condition, sex and extent of the disease in the subject and can be determined by one of skill in the art. The dosage can be adjusted by the individual physician monitoring the therapy.

Additional pharmaceutical methods may be employed to control the duration of action. Controlled release preparations may be achieved by the use of polymers to conjugate, complex or adsorb the glycosphingolipid.

In an exemplary embodiment, the invention provides a method of treating Parkinson's disease by providing neuroprotection from damage caused by toxic metabolites of dopamine. The method comprises administering to a subject in need thereof an amount of a glycolipid as set forth herein, which is sufficient to provide the neuroprotection. In an exemplary embodiment, the administration results in an amelioration of Parkinson's symptoms or a cure of the disease.

In another exemplary embodiment, the invention provides a method of binding a protein implicated in a disease state. Exemplary proteins include tau protein, beta-amyloid proteins, α-synuclein and huntingtin. The method comprises administering to a subject in need thereof an amount of a glycolipid as set forth herein, which is sufficient to protein implicated in the disease state. In an exemplary embodiment, the binding yields an amelioration or cure of the disease state by reducing or eliminating protein in the form in which it is implicated in the disease state.

Methods of Analyzing Glycosphingolipids and Identifying a Ganglioside Deficiency State in a subject A ganglioside deficiency state can be identified by assaying blood, plasma, CSF or other tissue samples from the subject for the pertinent ganglioside. A deficiency state exists when a particular ganglioside is absent or less than two-thirds that of an otherwise comparable control population. In some embodiments, the deficiency state exists when tissue levels of the pertinent ganglioside are one-half, one-quarter, one-tenth or one-twentieth of a normal, control, or reference level.

Many methods of analyzing biological samples for ganglioside and glycosphingolipid content are known to one of ordinary skill in the art. The use of such methods has been exemplified by Simpson, et al., *Nature Genetics* 36(11):1225 (2004) using HPLC-based methods developed by Neville, et al., *Anal Biochem.* 331(2):275-82 (2004) which are each incorporated herein by reference in their entirety, and particularly, with respect to such methods. These methods provide a rapid and sensitive method to both analyze and characterize the full complement of glycosphingolipid structures present in various cells and tissues. The method characterizes the oligosaccharides released from glycosphingolipids following ceramide glycanase digestion.

Additional methods for analyzing gangliosides are taught by Anumula and Dhume, *Glycobiology* 8:685 (1998), Svennerholm L, et al., *Biochim Biophys Acta* 617:97-109 (1980) and Wang B. et al., *Comp Biochem Physiol A Mol Integr Physiol* 119:435-9 (1998); and Wang B., e al., *Am J Clin Nutr.* 78(5):1024-9 (2003). Such methods can also be used to identify and quantify compounds for use according to the invention in tissue samples.

Glycolipid deficiency states suitable for treatment can also be identified by measuring the levels of the pertinent glycolipid in a sample from the subject and comparing the measured level with levels of the pertinent ganglioside measured or already established for suitable control populations as would be known to one of ordinary skill in the art. Referent levels of glycolipid in plasma for a control population have been reported previously (Simpson, Nature Genetics, 36: 1225-1229 (2004)).

It is contemplated that when used to treat various diseases such as cancer, atypical Parkinson's disease; Huntington's disease, multiple systems atrophy, GM3 synthase deficiency, GM2 synthase deficiency, hyperinsulinemia, hypoglycemia, hyperinsulinemia with hypoglycemis, a tauopathy, or another neurological disorder or condition associated with an increased aggregation of tau protein, the compounds of the invention can be combined with other therapeutic agents suitable for the same or similar diseases.

The compounds, antibodies and chemotherapeutic agents of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

In one embodiment, the treatment of the present invention involves the combined administration of a compound from Formula (1) to (10), an antibody and one or more chemotherapeutic agents. Preparation and dosing schedules for chemotherapy are also described in Chemotherapy Service Ed., M. C. Perry, Williams & Wilkins, Baltimore, Md. (1992). The chemotherapeutic agent may precede, or follow administration of the compound, the antibody or may be given simultaneously therewith.

A typical therapeutically effective dosage of a compound of the invention ranges from about 0.1 mg/kg to about 1000 mg/kg, preferably from 0.1 mg/kg to about 100 mg/kg, more preferably from about 0.1 mg/kg to about 30 mg/kg, more preferably from about 0.1 mg/kg to about 10 mg/kg, and more preferably 0.1 mg/kg to about 3 mg/kg. Advantageously, the compounds for use according to the invention, alone or as part of a pharmaceutical composition, maybe administered several times daily, and other dosage regimens may also be useful. A compound of the invention may be administered on a regimen in a single or multidose (e.g., 2 to 4 divided daily doses or applications). The regimen may be tailored over time according to the response of the subject. The dosage regimen may be hourly, daily, weekly, monthly, acute, subacute, subchronic or chronic. Up to 30 g (e.g., 1 to 2, 2 to 5, 5 to 10, 10 to 20, or 20 to 30 g), for instance, may be administered in one dose.

The effectiveness of the compounds for use according to the invention may be determined using screening protocols known in the art. The biological properties of the compounds for use according to the invention can be readily characterized by methods that are well known in the art including, for example, in vitro screening protocols (e.g., cell cultures and in vivo studies for effectiveness). Exemplary methods for identifying or screening suitable compounds for use according to the invention are set forth below.

The invention is further described with reference to the following Examples. The Examples are provided for the purpose of illustration only and the invention not be construed as being limited to these Examples, but rather should be construed to encompass any and all variations which become evident as a result of the teaching provided herein.

Example 1

Synthesis of [5-N-acetyl-α-neuraminyl)-(2→3)]-[β-D-galactopyranosyl-(1→4)-β-D-glucopyranose] by Fermentation The synthesis of this compound uses the process described by Samain (Samain and Priem, Method for Producing Oligopolysaccharides. WO 01/04341 (2001); Priem, Glycobiology, 12:235 (2002); Cottaz, EP Application No. 06291569.9 (2006)) with *E. coli* JM107-*nanA*-(Nst-01, pBBnsy) strain using lactose and sialic acid (Kok, J Chem Soc Perkin Trans, 1:2811-2815 (1996)) acid as exogeneous acceptors.

*E. coli* JM107-nanA-(Nst-01, pBBnsy) strain was grown at low cell density culture in shake flask fermentation. When the OD540 is about 1, isopropyl 1-thio-β-galactopyranoside (IPTG) and the substrates Neu5Ac and lactose (2 equivalents) were added via a sterile filter and the culture is shaken at 28° C. for 16 hr. After 16 hr, the cells were recovered by centrifugation at 8000 g and 4° C. for 10 min. The supernatant was separated for further TLC analysis while the pellet is resuspended in $H_2O$ and boiled for 30 min. The resulting suspension was again centrifuged (8000 g, 4° C. for 10 min). The supernatant was mixed with activated charcoal, filtered through Celite and is washed with distilled water. The adsorbed oligosaccharides were eluted with 50% aq. EtOH. The oligosaccharide was further purified using a DOWEX exchange ions resin (DOWEX 1×4 50) and silica gel column chromatography. The solution of product eluted from the silica gel chromatography was evaporated to dryness to yield a solid that is examined by NMR and MS to confirm the structure.

Example 2

Synthesis of 1-Fluoro-[(5-N-acetyl-α-neuraminyl)-(2→3)]-[β-D-galactopyranosyl-(1→4)-β-D-glucopyranoside]

The [5-N-acetyl-α-neuraminyl)-(2→3)]-[β-D-galactopyranosyl-(1→4)-β-D-glucopyranose], and DMAP are dissolved in pyridine. Acetic anhydride was added dropwise and then the reaction mixture is stirred for 2 days. The reaction mixture was concentrated and the residue treated with methanol. After 30 min, the reaction mixture was concentrated again, the residue dissolved in ethyl acetate and the organic solution washed with water, 5% citric acid in water, water and brine. The organic solution was dried with sodium sulfate, filtered and concentrated to dryness yielding a solid used directly for the next step.

The solid is cooled to −30° C. and then hydrogen fluoride-pyridine was added. The reaction mixture was stirred for 1 hr allowing the reaction to slowly warm to room temperature and then for 4 hrs at room temperature. The reaction mixture was cooled to −10° C. and is then slowly added to a cold solution of 6 N NaOH. Sodium carbonate is then carefully added until the pH of the solution is about 8.0. The solution was then extracted with $CH_2Cl_2$ (three times) and the combined organic layers dried over sodium sulfate. Concentration provided a solid used directly for the next step.

The solid was dissolved in anhydrous methanol and sodium methoxide in methanol is added. The reaction mixture was stirred overnight, treated with Dowex HCR-W2 resin ($H^+$), the resin was removed by filtration and the filtrate concentrated to dryness to yield a solid. The product is characterized by NMR and MS.

Example 3

Synthesis of [(5-N-acetyl-α-neuraminyl)-(2→3)]-[β-D-galactopyranosyl-(1→4)-β-D-glucopyranosyl-β-(1→1')-D-erythro-sphingosine]

The compound 1-fluoro-[(5-N-acetyl-α-neuraminyl)-(2→3)]-[β-D-galactopyranosyl-(1→4)-β-D-glucopyranoside] and D-erythro-sphingosine are coupled using the procedure as described in Vaughan, J Am Chem Soc, 128:6300-6301 (2006). The reaction was performed in 25 mM NaOAc (pH 5.0) containing 0.2% Triton X-100. A typical reaction mixture contained approximately 10 mM 1-fluoro-[(5-N-acetyl-α-neuraminyl)-(2→3)]-[β-D-galactopyranosyl-(1→4)-β-D-glucopyranoside], 20 mM of the acceptor D-erythro-sphingosine, and 0.5 mg/mL of the appropriate EGC mutant in a total reaction volume. When completed, the product was purified using reversed phase (C-18) chromatography, the eluted product was concentrated to dryness, dissolved in water and freeze-dried to yield a white solid. The product is analyzed by NMR and MS.

Example 4

Synthesis of [(5-N-acetyl-α-neuraminyl)-(2→3)]-[β-D-galactopyranosyl-(1→4)-β-D-glucopyranosyl]-β-(1→1')-[2-N-stearoyl-D-erythro-sphingosine]

The [(5-N-acetyl-α-neuraminyl)-(2→3)]-[β-D-galactopyranosyl-(1→4)-β-D-glucopyranosyl-β-(1→1')-D-erythro-sphingosine] was dissolved in anhydrous methanol that contains triethylamine. Stearic anhydride was added as a solid to the reaction mixture and the reaction stirred for 24 hrs. The product was purified using silica gel chromatography eluting the product with $CHCl_3/CH_3OH$. Concentration of the product fractions provides a solid that is analyzed by NMR and MS.

Example 5

Synthesis of (β-D-galactopyranosyl)-(1→3)-(β-D-2-N-acetamido-galactopyranosyl)]-β-(1→4)-[(5-N-acetyl-α-neuraminyl)]-(2→3)-(β-D-galactopyranosyl)-(1→4)-β-D-glucopyranose by Fermentation The synthesis of this compound used the process described by Samain (Samain and Priem, Method for Producing Oligopolysaccharides. WO 01/04341 (2001); Priem, Glycobiology, 12:235 (2002); Cottaz, EP Application No. 06291569.9 (2006)) with *E. coli* JM107-nanA-(Nst-01, pBBnsy) strain using lactose.

*E. coli* JM107-nanA-(Nst-01, pBBnsy) strain is grown at low cell density culture in shake flask fermentation. When the OD540 was about 1, isopropyl 1-thio-β-galactopyranoside (IPTG) and the substrates Neu5Ac and lactose (2 equivalents) were added via a sterile filter and the culture was shaken at 28° C. for 16 hr. After 16 hr, the cells were recovered by centrifugation at 8000 g and 4° C. for 10 min. The supernatant was separated for further TLC analysis while the pellet is resuspended in $H_2O$ and boiled for 30 min. The resulting suspension is again centrifuged (8000 g, 4° C. for 10 min). The supernatant was mixed with activated charcoal, filtered through Celite and was washed with distilled water. The adsorbed oligosaccharides were eluted with 50% aq. EtOH. The oligosaccharide was further purified using a DOWEX exchange ions resin (DOWEX 1×4 50) and silica gel column chromatography. The solution of product eluted from the silica gel chromatography was evaporated to dryness to yield a solid that is examined by NMR and MS to confirm the structure.

Example 6

Synthesis of 1-Fluoro-[(β-D-galactopyranosyl)-(1→3)-(β-D-2-N-acetamido-galactopyranosyl)]-β-(1→4)-[(5-N-acetyl-6-deoxy-α-neuraminyl)]-(2→3)-(β-D-galactopyranosyl)-(1→4)-β-D-glucopyranoside]

The (β-D-galactopyranosyl)-(1→3)-(β-D-2-N-acetamido-galactopyranosyl)]-β-(1→4)-[(5-N-acetyl-α-neuraminyl)]-(2→3)-(β-D-galactopyranosyl)-(1→4)-β-D-glucopyranose, and DMAP were dissolved in pyridine. Acetic anhydride was added dropwise and then the reaction mixture is stirred for 2 days. The reaction mixture was concentrated and the residue treated with methanol. After 30 min, the reaction mixture was concentrated again, the residue dissolved in ethyl acetate and the organic solution washed with water, 5% citric acid in water, water and brine. The organic solution was dried with sodium sulfate, filtered and concentrated to dryness yielding a solid used directly for the next step.

The solid was cooled to −30° C. and then hydrogen fluoride-pyridine was added. The reaction mixture was stirred for 1 hr allowing the reaction to slowly warm to room temperature and then for 4 hrs at room temperature. The reaction mixture was cooled to −10° C. and was then slowly added to a cold solution of 6 N NaOH. Sodium carbonate was then carefully added until the pH of the solution was about 8.0. The solution was then extracted with $CH_2Cl_2$ (three times) and the combined organic layers dried over sodium sulfate. Concentration provides a solid used directly for the next step.

Example 7

Synthesis of [(β-D-galactopyranosyl)-(1→3)-(β-D-2-N-acetamido-galactopyranosyl)]-β-(1→4)-[(5-N-acetyl-α-neuraminyl)]-(2→3)-(β-D-galactopyrano-syl)-(1→4)-(β-D-glucopyranosyl)-β-(1→1')-O-[(1R,2R)-2-amino-1-(1,3-dioxolan-2 yl)-propane-1,3-diol)]

The compound 1-fluoro-[(β-D-galactopyranosyl)-(1→3)-(β-D-2-N-acetamido-galactopyranosyl)]-β-(1→4)-[(5-N-acetyl-α-neuraminyl)]-(2→3)-(β-D-galactopyranosyl)-(1→4)-β-D-glucopyranoside] and (1R,2R)-2-amino-1-(1,3-dioxolan-2 yl)-propane-1,3-diol) is coupled using the procedure described in Example 3 using a mutant EGC enzymes (Vaughan, J Am Chem Soc, 128:6300-6301 (2006)). The reaction is performed in 25 mM NaOAc (pH 5.0) containing 0.2% Triton X-100. A typical reaction mixture contained approximately 10 mM 1-fluoro-[(5-N-acetyl-α-neuraminyl)-(2→3)]-[β-D-galactopyranosyl-(1→4)-β-D-glucopyranoside], 20 mM of the acceptor D-erythro-sphingosine, and 0.5 mg/mL of the appropriate EGC mutant in a total reaction volume. When completed, the product is purified using reversed phase (C-18) chromatography, the eluted product is concentrated to dryness, dissolved in water and freeze-dried to yield a white solid. The product is analyzed by NMR and MS.

Example 8

Synthesis of [(5-N-acetyl-α-neuraminyl)-(2→3)]-[β-D-galactopyranosyl-(1→4)-β-D-glucopyranosyl]-β-(1→1')-O—[N-((2R,3S,E)-1,3-dihydroxy-5-phenyl-pent-4-ene-2-yl)-stearamide]

The [(5-N-acetyl-α-neuraminyl)-(2→3)]-[β-D-galacto-pyranosyl-(1→4)-β-D-glucopyranosyl]-β-(1→1')-O-[2-N-stearoyl-D-erythro-sphingosine], a water stable Grubb's catalyst (Hong, J Am Chem Soc, 128:3508-3509 (2006) and styrene is stirred in water/methanol. The reaction mixture is then concentrated to dryness and purified by silica gel chromatography using $CHCl_3/CH_3OH$. The eluted product fractions is concentrated to afford the product as a solid that was characterized by NMR and MS.

Example 9

Synthesis of [(β-D-galactopyranosyl)-(1→3)-(β-D-2-N-acetamido-galactopyranosyl)]-β-(1→4)-[(5-N-acetyl-α-neuraminyl)]-(2→3)-(β-D-galactopyrano-syl)-(1→4)-(β-D-glucopyranosyl)-β-(1→1')-O-[(2R,3R,E)-2-N-stearamido-4-(dioctylamino)-6-phenylhex-5-ene-1,3-diol]

The (5-N-acetyl-α-neuraminyl)-(2→3)-(β3-D-galactopy-ranosyl)-(1→4)-(β-D-glucopyranosyl)-β-(1→1')-O-[(1R,2R)-2-amino-1-(1,3-dioxolan-2 yl)-propane-1,3-diol)]-β-(1→1')-O-[(2R,3R,E)-2-amino-4-(dioctylamino)-6-phenylhex-5-ene-1,3-diol] is dissolved in anhydrous methanol that contains triethylamine. Stearic anhydride is added as a solid to the reaction mixture and the reaction stirred for 24 hrs. The product is purified using silica gel chromatography eluting the product with $CHCl_3/CH_3OH$. Concentration of the product fractions provides a solid that is analyzed by NMR and MS.

The solid is dissolved in methanol, tartaric acid, and water and stirred at room temperature for 24 hrs. The reaction mixture is neutralized with sodium bicarbonate the product extracted with $CH_2Cl_2$ (3 times). The organic layers are combined and dried with $NaSO_4$, filtered and concentrated to dryness. The solid is used directly for the next step.

The product from the previous step (20 mg, 0.01 mmol) and dioctylamine (6 mg, 0.024 mmol) are dissolved in dimethylformamide (DMF) at room temperature. A solution of trans-2-phenylvinylboronic acid (9 mg, 0.045 mmol) dissolved in methanol (5 mL) is then added. The resulting solution is stirred at room temperature for three days. The reaction mixture is then concentrated to dryness on a rotovap and the residue purified by solid phase extraction using a 1 g HAX cartridge. The eluant is then purified using HPLC to afford the product as a solid that is characterized by NMR and MS.

Example 10

In Vitro Cell Proliferation

The efficacy of compounds of formula (1)-(10) compounds alone and in combination with a kinase inhibitor is measured by a cell proliferation assay employing the following protocol (Promega Corp. Technical Bulletin TB288; Mendoza et al (2002) Cancer Res. 62:5485-5488). An aliquot of 100 μL of cell culture containing about $10^4$ cells (from the ATCC or DZM such as A549, NCI-H441, NCI-1650, NCI-1975, PC-3, DiFi, HN5, SKBR3, MCF-7, HCT-116, CCL-221, NCI-H125, SK-OV-3, MIA PaCa-2, T-47D) in medium are deposited in each well of a 384-well, opaque-walled plate. Control wells are prepared containing medium and without cells. The compound are added to the experimental wells and incubated for 3-5 days. The plates are equilibrated to room temperature for approximately 30 minutes and a volume of CellTiter-Glo Reagent equal to the volume of cell culture medium present in each well is added. The contents are mixed for 2 minutes on an orbital shaker to induce cell lysis. The plate is incubated at room temperature for 10 minutes to stabilize the luminescence signal and the luminescence recorded and reported in graphs as RLU=relative luminescence units.

Alternatively, cells are seeded at optimal density in a 96 well plate and incubated for 4 days in the presence of test compound. Alamar Blue™ is subsequently added to the assay medium, and cells are incubated for 6 h before reading at 544 nm excitation, 590 nm emission. $EC_{50}$ values are calculated using a sigmoidal dose response curve fit.

Example 11

Identification of Glycolipids Capable of Cell Growth Inhibition Against Lung Cancer Cells, Ovarian Cancer Cells and Colon Cancer Cells As cancer cell lines, human lung cancer A549 cells (ATCC No. CCL-185), human ovarian cancer SK-OV-3 cells (ATCC No. HTB-77), and human colon cancer HCT 116 cells (ATCC No. CCL-247) are used. For the culture of A549 cells, Nutrient Mixture F-12K medium containing 10% fetal bovine serum, 100 units/mL penicillin, and 100 μg/mL streptomycin are used. For the culture of SK-OV-3 cells and HCT 116 cells, McCoy's 5A medium containing 10% fetal bovine serum, 100 units/mL penicillin, and 100 μg/mL streptomycin are used. The cells are cultured at 37° C. in a 5% carbon dioxide atmosphere.

A549 cells (1000 cells/well), SK-OV-3 cells (2000 cells/well), or HCT 116 cells (1000 cells/well) are seeded in each well of 96-well plates, and cultured overnight. Test compounds of formula (1), (2), (3), (4), (5), (6), (7), (8), (9) or (10) to be tested are applied to the appropriate wells at a variety of concentrations and at various time points beginning at 24, 18, 12, 6, and 0 hrs prior to kinase inhibitor addition at three different concentrations. The cells are further cultured for 72 hours. Fifty μL of labeling mixture of Cell Proliferation Kit II (XTT) are added to each well, and the plates are incubated at 37° C. After 1 to 3 hours, the absorbance at 490 nm (reference wavelength: 655 nm) is measured with a plate reader. Growth ratios of the cells in the wells treated with the test compounds are calculated based on the growth ratio of the cells in the control well treated with solvent (dimethyl sulfoxide (DMSO)) for 72 hours, which was defined as 100%. From a plot of test compound concentrations and the cell growth ratios at the concentrations, the concentration of 50% growth inhibition, the $GI_{50}$ value, are calculated.

Example 12

Identification of Glycolipids Capable of Cell Growth Inhibition Against Pancreatic Cancer Cells, Cervical Cancer Cells, Breast Cancer Cells, Prostate Cancer Cells, Skin Cancer Cells, Head and Neck Cancer Cells, Renal Cancer Cells and Liver Cancer Cells As cancer cell lines, human pancreatic cancer MIA PaCa-2 cells (JCRB No. 0070), human cervical cancer HeLa cells (ATCC No. CCL-2), human breast cancer MDA-MB-468 cells (ATCC No. HTB-132), human prostate cancer DU 145 cells (ATCC No. HTB-81), human skin cancer SK-MEL-28 cells (ATCC No. HTB-72), human head and neck cancer KB cells (JCRB No. 9027), human renal cancer 786-0 cells (ATCC No. CRL-1932), and human liver cancer Hep G2 cells (ATCC No. HB-8065) are used. The cells are cultured at 37° C. in a 5% carbon dioxide atmosphere (except for the human breast cancer MDA-MB-468 cells, which are cultured under the condition at 37° C.) by using the mediums mentioned below, respectively.

Cell Medium: Human pancreatic Minimum Essential Medium (MIA PaCa-2) containing 10% fetal bovine serum, 0.1 mmol/L MEM Non-Essential Amino Acids Solution, 100 units/mL penicillin and 100 μg/mL streptomycin; Human cervical cancer Minimum Essential Medium containing 10% fetal bovine serum, 0.1 mmol/L MEM Non-Essential Amino Acids Solution, 100 units/mL penicillin and 100 μg/mL streptomycin; Human breast cancer Leibovitz's L-15 Medium (MDA-MB-468) containing 10% fetal bovine serum, 100 units/mL penicillin, and 100 μg/mL streptomycin; Human prostate cancer Minimum Essential Medium containing 10% fetal bovine serum, 0.1 mmol/L MEM Non-Essential Amino Acids Solution, 1 mmol/L Sodium Pyruvate Solution, 100 units/mL penicillin and 100 μg/mL streptomycin; Human skin cancer Minimum Essential Medium (SK-MEL-28) containing 10% fetal bovine serum, 0.1 mmol/L MEM Non-Essential Amino Acids Solution, 100 units/mL penicillin and 100 μg/mL streptomycin; Human head and neck Minimum Essential Medium (KB cell 11095-080) containing 10% fetal bovine serum, 0.1 mmol/L MEM Non-Essential Amino Acids Solution, 100 units/mL penicillin and 100 μg/mL streptomycin; Human renal cancer RPMI 1640 Medium (786-O cell) containing 10% fetal bovine serum, 10 mmol/L HEPES Buffer Solution, 1 mmol/L Sodium Pyruvate Solution, 4.5 g/L D-(+)-Glucose Solution, 100 units/mL penicillin and 100 μg/mL streptomycin; Human liver cancer Minimum Essential Medium (Hep G2 cell) containing 10% fetal bovine serum, 0.1 mmol/L MEM Non-Essential Amino Acids Solution, 1 mmol/L Sodium Pyruvate Solution, 100 units/mL penicillin and 100 μg/mL streptomycin.

In the same manner as that in Example 9, the cells are seeded (500 to 4000 cells/well, respectively) in each well of 96-well plates, and the growth ratios of the cells treated with test compounds of formula (1), (2), (3), (4), (5), (6), (7), (8), (9) or (10) are applied to the appropriate wells at a variety of concentrations and at various time points beginning at 24, 18, 12, 6, and 0 hrs prior to kinase inhibitor addition at three different concentrations. The measurement of absorbance is performed at 1.5 to 3 hours after the addition of the XTT labeling mixture. From a plot of test compound concentra-

Examples 13

Identification of Glycolipids Capable of Preventing Tumor Growth in a Breast Cancer Cell Xenograft Mouse Model In an exemplary model system, nude (nu/nu) mice are inoculated with MDA-MB-231 cells (human breast carcinoma) ($10^6$ cells in 0.2 mL) s.c. in the right flank of the animals. The tumors are staged to 200 mm$^3$ and then treatment with the test compound (1, 30 or 100 mg/Kg; IV or sc) and kinase inhibitor (IV or sc)(e.g., lapatinib). Tumor volumes are obtained every other day and the animals are sacrificed after 2 weeks of treatment. The tumors are excised, weighed and paraffin embedded. Histological sections of the tumors are analyzed, for example, by H and E, anti-CD31, Ki-67, TUNEL, and CD68 staining.

Examples 14

Identification of Glycolipids Capable of Treating Established Burkitt's Lymphoma in SCID Mice A xenotransplant model of the Raji Burkitt's lymphoma in SCID mice is used. Raji cells after s.c. injection cause locally growing tumors. Treatment is started when the tumors have reached a size of 5 mm in diameter. At days 0, 7, and 15, cohorts of five mice receive i.v. either PBS (control group) or in vitro preactivated human PBLs. Four hrs after each PBL inoculation, the mice are treated via tail vein injection either with no antibody, or the following: compounds of the invention alone; compound (1, 50 or 100 mg/Kg) and kinase inhibitor; or compound (1, 50 or 100 mg/Kg) 3 hrs prior to administration of kinase inhibitor. Tumor size is measured using a caliper every 2$^{nd}$ day. Animals are followed until the s.c. tumors reached a maximal tolerated size of 15 mm in diameter and are then killed by cervical dislocation. The days of sacrifice are recorded and are used for survival time analysis.

Examples 15

Identification of Glycolipids Capable of Enhancing the Effects of EGFR Kinase Inhibitors on the Survival of Mice after the Orthotopic Transfer of Non-Small Lung Cancer Cells The compounds of the invention were dissolved in PBS and administered in Gefitinib (AstraZeneca Pharmaceuticals) was dissolved in vehicle containing 1% Tween 80. AEE788 (Novartis Pharmaceuticals) was dissolved in vehicle containing 90% polyethylene glycol 300 and 10% 1-methyl-2-pyrrolidinone. Five days after the implantation of the NCI-H441 or PC14-PE6 tumor cells into their lungs, mice (8-10 per group) are randomized into treatment groups and treated with: compounds of the invention (once daily, s.c. or oral gavage; 1-100 mg/Kg); an EGFR1 inhibitor (e.g., gefitinib, po, once daily, 50 mg/Kg; AEE788 po, 3×weekly, 50 mg/Kg; lapatinib, p.o., once daily, 50 mg/Kg; erlotinib, p.o., once daily, 50 mg/Kg); or compounds of the invention (once daily, s.c. or oral gavage; 1-100 mg/Kg) in combination with an EGFR1 inhibitor (selected from gefitinib, p.o., once daily, 50 mg/Kg; AEE788 po, 3×weekly, 50 mg/Kg; lapatinib, p.o., once daily, 50 mg/Kg or erlotinib, p.o., once daily, 50 mg/Kg) or vehicle control. All of the mice are killed and autopsied when control animals become moribund and primary lung tumor weight (total tumor-bearing lung weight minus the normal lung weight of 0.17 g), incidence and volume of pleural effusion, and the presence of metastasis are measured.

Example 15

Ability of Glycolipids to Modify Glucose Transport

Glucose transport are determined in 3T3-L1 adipocytes or primary human adipocytes as uptake of 2-deoxy-D-[1-$^3$H] glucose by the method of Frost, J Biol Chem, 262:9872-9876 (1987). Cells are grown on 13 mm plastic coverslips in 24-well culture dishes. The cells are treated with the compounds of formula (1), (2), (3), (4), (5), (6), (7), (8), (9) or (10) at concentrations of 1, 10, 50, 100 µM) and incubated with the cells for at various time points from 0, 30 min, 1 hr and 2 hrs prior to addition of 2-deoxy-D-[1-$^3$H]glucose. The 2-deoxy-D-[1-$^3$H]glucose is then added to a final concentration of 50 mM (0.5 mCi/mL) and the cells are incubated for 6 min. Glucose uptake is stopped by rinsing the coverslips in three successive solutions of ice-cold buffer. Non-specific uptake is determined in the presence of 25 mM of cytochalasin B. Coverslips are transferred to scintillation vials and the cells are dissolved in 1% SDS. Radioactivity is measured after adding 5 mL of scintillation fluid.

Example 16

Ability of Glycolipids to Inhibit the Insulin Receptor

Human Lymphoid cells (IM9) are grown in culture and the insulin receptor isolated as described (Nojiri, J Biol Chem, 266:4531-4537 (1991)). Compounds of formula (1), (2), (3), (4), (5), (6), (7), (8), (9) or (10) at concentrations of 0, 0.1, 1, 10, 30, 100 and 200 µM are added to a solution (50 mM HEPES, pH 7.4, 0.1% (v/v) Triton X-100; 30 µL) containing the purified insulin receptor. Insulin (26.3 IU/mg; 5 µL) and MnCl$_2$ (30 mM, 10 µL) are then added to each tube and incubated at room temperature for 1 hr. Phosphorylation is initiated by adding ATP-[γ-$^{32}$P] (5 µL; 25 µCi) and the reaction mixture incubated at room temperature for 10 min. The reaction is terminated by the addition of Laemmli's buffer (Laemmli, Nature, 227:680-685 (1970)) containing DTT (75 mg/mL) and heating in boiling water for 3 min. The phosphoproteins are separated by SDS-PAGE, the gel stained with Cibracron blue and an autoradiograph taken. The β-subunit of the insulin receptor is cut from the gel and the amount of radioactivity quantified using a liquid scintillation counter. The amount of inhibition is then plotted.

Example 17

Ability of Glycolipids to Inhibit the Phosphorylation of the Insulin Receptor in Mice Experiments are performed in mice fasted for 14 h. The compounds of Formula (1), (2), (3), (4), (5), (6), (7), (8), (9) or (10) are administered IV, SC, oral gavage or IP to the mice at doses of 0, 0.1, 1, 10, 30 or 100 mg/Kg. Insulin (5 units per animal) is administered at 0 min, 30 min, 1 hr, 2 hr, 6 hr, 12 hr or 24 hr after compound administration through the inferior vena cava under anesthesia. Two minutes after injection, hind limb muscle and adipose tissue are removed and incubated for 30 min on ice with lysis buffer (PBS, pH 7.4/1% Nonidet P-40/0.5% sodium a deoxocholate/0.1% SDS/1 mM PMS/10 mM sodium orthovanadate/3 g/ml aprotinin). Lysates are immunoprecipitated with an anti-insulin receptor subunit antibody. Immunoprecipitated samples are subjected to SDS-PAGE and then transferred to nitrocellulose membranes. The blots are probed sequentially, first with an antiphospho-tyrosine antibody (PY99) and then with an anti-insulin receptor-subunit antibody. Blots are developed by a chemiluminescence detection system. The mice may be normal mice or mice that contain one or more genes that have been deleted, mutated, knocked-in or a combination thereof.

Example 18

Ability of Glycolipids to Modify Glucose Tolerance, Insulin Tolerance and Hormone Levels in Mice with and without a High-Fat Diet Glucose and insulin tolerance tests are performed in fasted mice (13-15 h) with i.p. injections of glucose (2 g of glucose per kg of body weight) or insulin (0.75 units of insulin per kg of body weight), respectively. For the glucose tolerance test, compounds of Formula (1), (2), (3), (4), (5), (6), (7), (8), (9) or (10) are administered by IV, SC, oral gavage or IP at a dose of 0, 0.1, 1, 10 and 100 mg/Kg at timepoints of 0 min, 30 min, 1 hr, 2 hr, 6 hr, 12 hr or 24 hrs prior to glucose injection. Blood glucose values are measured immediately before and 15, 30, 60, and 120 min after glucose injection. For the insulin tolerance test, compounds of Formula (1), (2), (3), (4), (5), (6), (7), (8), (9) or (10) are administered by IV, SC, oral gavage or IP at a dose of 0.1, 1, 10 and 100 mg/Kg at timepoints of 0 min, 30 min, 1 hr, 2 hr, 6 hr, 12 hr or 24 hrs prior to insulin injection. Blood glucose levels are measured immediately before and 15, 30, and 60 min after insulin injection. To induce glucose intolerance, 6- to 8-week-old mice are placed on a 45% high-fat diet (commercial preparation) for 10 weeks (Steppan, Nature, 409:307-312 (2001)). The mice may be normal mice or mice that contain one or more genes that have been deleted, mutated, knocked-in or a combination thereof.

Example 19

Ability of Glycolipids to Improve Hypoglycemia by Initiating a Hyperinsulinemic-Hypoglycemia State in Normal Mice Animals are fasted overnight. The compounds of Formula (1), (2), (3), (4), (5), (6), (7), (8), (9) or (10) are administered via IV, SC, oral gavage or IP at a dose of 0, 0.1, 1, 10, 30 or 100 mg/Kg. A 120-minute hyperinsulinemic-hypoglycemic clamp is conducted with a continuous infusion of human insulin at a rate of 15 pmol/Kg/min or higher to create a hyperinsulinemic hypoglycemic state that is started at 0 min, 30 min, 1 hr, 2 hr, 6 hr, 12 hr and 24 hrs after compound administration. Blood samples (20 µL) are collected at 20- to 30-minute intervals for the immediate measurement of plasma glucose concentration. Insulin-stimulated whole-body glucose flux is estimated using a prime-continuous infusion of HPLC-purified [3-$^3$H]glucose (10 µCi bolus, 0.1 µCi/min) throughout the clamps. To estimate insulin-stimulated glucose transport activity in individual tissues, 2-de-oxy-D[1-$^{14}$C]glucose (2-[14C]DG) is administered as a bolus (10 µCi) at 45 minutes before the end of clamps. Blood samples (20 µL) are taken at 77, 80, 85, 90, 100, 110, and 120 minutes after the start of clamps for the determination of plasma [$^3$H]glucose, $^3$H$_2$O, and 2-[$^{14}$C]DG concentrations. Additional blood samples (10 µL) are collected before the start and at the end of clamps for measurement of plasma insulin concentrations. All infusions are done using microdialysis pumps. At the end of clamps, animals are anesthetized with sodium pentobarbital injection. Within 5 minutes, four muscles (soleus, gastrocnemius, tibialis anterior, and quadriceps) from both hindlimbs, epididymal adipose tissue, and liver are taken. Each tissue, once exposed, is dissected out within 2 seconds, frozen immediately using liquid N$_2$-cooled aluminum blocks, and stored at −70° C. for later analysis.

Plasma glucose concentration during clamps are analyzed using 10 µL plasma by a glucose oxidase method on a Beckman glucose analyzer II. Plasma insulin concentration are measured by RIA using kits. For the determination of plasma [3-$^3$H]glucose and 2-[$^{14}$C]DG concentrations, plasma is deproteinized with ZnSO$_4$ and Ba(OH)$_2$, dried to remove $^3$H$_2$O, resuspended in water, and counted in scintillation fluid on dual channels for separation of $^3$H and $^{14}$C. The plasma concentration of $^3$H$_2$O is determined by the difference between $^3$H counts without and with drying. For the determination of tissue 2-[$^{14}$C]DG-6-phosphate (2-DG-6-P) content, tissue samples are homogenized, and the supernatants are subjected to an ion-exchange column to separate 2-DG-6-P from 2-DG (Ohshima, Am J Physiol, 246:E193-E197 (1984)). The radioactivity of 3H in muscle glycogen is determined by digesting muscle samples in KOH and precipitating glycogen with ethanol (Kim, Diabetes, 45:446-453 (1996)). Skeletal muscle glycogen synthase activity is measured using $^{14}$C-UDPG.

Example 20

Ability of Glycolipids to Improve Hypoglycemia in Mice Containing Mutations or Deletions in Genes Related to Familial Hyperinsulinemia The compounds of Formula (1), (2), (3), (4), (5), (6), (7), (8), (9) or (10) are administered to rats via i.v., s.c., p.o. (oral gavage), or i.p. at doses of 0, 0.1, 1, 10, 30 and 100 mg/Kg. Blood glucose levels and insulin levels are measured by drawing blood from the animal at 0, 30 min, 1 hr, 1.5 hrs, 2 hrs, 4 hrs, 6 hrs, 12 hrs and 24 hrs after administration of the compound. Whole blood is assayed for glucose content using the glucose dehydrogenase based enzymatic assay and quantitated using the Hemocue glucose meter. Insulin levels are assayed in 15 µL of serum using the Rat Insulin RIA kit according to manufacturer's procedure. Intraperitoneal glucose tolerance tests are made on 12- to 20-week-old mice, after 16 hr fast. Animals are injected i.p. with glucose (1 g/Kg). Blood is isolated from the tail vein at times indicated and assayed for glucose content as described above. Insulin content is assayed in isolated islets of equal diameter (~100 µm). Islets are sonicated in distilled water, then pelleted for 5 min at 1,000×g. Supernatant is removed and diluted 1:6,000 for RIA as described above.

Exendin-(9-39) Significantly Raises Fasting Blood Glucose Levels in SUR-1−/− Mice Example 21

Ability of Glycolipids to Raise Fasting Blood Glucose Levels in SUR-1−/− Mice

Twelve-18 week old male SUR-1−/− and wildtype littermates undergo a baseline evaluation including fasting blood glucose measurements and oral glucose tolerance testing, followed by randomization to treatment with compounds of Formula (1), (2), (3), (4), (5), (6), (7), (8), (9) or (10) (0, 0.1, 1, 10, 30 or 100 mg/Kg/day; i.v., s.c., p.o. (oral gavage) or i.p.) or vehicle (0.9% NaCl, 1% BSA). Fasting blood glucose levels are determined after an overnight fast on days 3 and 7 after initiation of the study. In addition, oral glucose tolerance and insulin sensitivity are evaluated during treatment.

Example 22

Ability of Glycolipids to Modify the Insulin Secretion, In Vitro

Pancreatic islets (10 per well), isolated as described in Koster, Proc Natl Acad Sci USA, 99: 16992-16997 (2002), are incubated in glucose-free DMEM supplemented with D-(+)-glucose (1, 7, or 16.7 mM) and either gliblenclamide (1 µM), diazoxide (250 µM) or one or more of the compounds of Formula (1), (2), (3), (4), (5), (6), (7), (8), (9) or (10) (0.1, 1, 10, 30 and 100 µM), as indicated. Alternatively, the islets are first incubated with the compounds of Formula (1), (2), (3), (4), (5), (6), (7), (8), (9) or (10) (0.1, 1, 10, 30 and 100 µM) for 0, 30 min, 1 hr, 2 hrs, 4 hrs or 6 hrs prior to glucose, gliblenclamide or diazoxide addition. Islets are incubated for 60 min at 37° C., medium removed and assayed for insulin content with Rat Insulin RIA kit. Pancreatic Islets may be isolated from normal or genetically modified animals or humans.

Example 23

Effect of Glycolipids in Regulating Insulin and Plasma Glucose Levels in HI Patients After an overnight fast, subject receives an intravenous infusion or subcutaneous injection of a compound selected from Formula (1), (2), (3), (4), (5), (6), (7), (8), (9) or (10) (1, 30 or 100 mg/Kg/day). On the second day, the subject is fasted overnight. Blood samples for glucose, insulin, C-peptide, and glucagon are obtained at different intervals after compound administration.

Example 24

Identification of Glycolipids Capable of Enhancing the Anti-Proliferative Activity of Rituxin using Non-Hodgkin's Lymphoma Cells Cultured from Patients Cancer cell samples are obtained from the affected individual from peripheral blood or bone marrow aspirates. In this examples, either B-cell CLL or MCL cells, depending on the malignancy being studies, were enriched using immunomagnetic sorting (Decker, Blood, 95:999-1006 (2000)). The cells are then cultured in RPMI 1640, supplemented with 30% autologous serum, 50 IU/mL penicillin/streptomycin, glutamine, CpG oligonucleotide DSP30, IL-2 and mercaptoethanol. Cells are plated in 96 well dishes and growth for 48 hrs. Cells are then resuspended in human serum and culture medium and the compound of formula (1), (2), (3), (4), (5), (6), (7), (8), (9) or (10) to be tested is applied to the culture at a variety of concentrations at various time points beginning at 24, 18, 12, 6, and 0 hrs prior to antibody addition (Rituxan). The Rituxan (anti-CD20) is then added and the cells incubated for 24 hrs. Dead and viable cells are discriminated by Annexin V/propidium iodide staining and assessed by flow cytometry.

Example 26

Identification of Glycolipids Capable of Cell Growth Inhibition Against Lung Cancer Cells, Breast, Ovarian Cancer Cells and Colon Cancer Cells As cancer cell lines, MCF7, human lung cancer A549 cells (ATCC No. CCL-185), human ovarian cancer SK-OV-3 cells (ATCC No. HTB-77), and human colon cancer HCT 116 cells (ATCC No. CCL-247) are used. For the culture of A549 cells, Nutrient Mixture F-12K medium containing 10% fetal bovine serum, 100 units/mL penicillin, and 100 µg/mL streptomycin are used. For the culture of SK-OV-3 cells and HCT 116 cells, McCoy's 5A medium containing 10% fetal bovine serum, 100 units/mL penicillin, and 100 µg/mL streptomycin are used. The cells are cultured at 37° C. in a 5% carbon dioxide atmosphere.

A549 cells (1000 cells/well), SK-OV-3 cells (2000 cells/well), or HCT 116 cells (1000 cells/well) are seeded in each well of 96-well plates, and cultured overnight. Test compounds of formula (1), (2), (3), (4), (5), (6), (7), (8), (9) or (10) to be tested are applied to the appropriate wells at a variety of concentrations and at various time points beginning at 24, 18, 12, 6, and 0 hrs prior to antibody addition at three different concentrations. The cells are further cultured for 72 hours. Fifty µL of labeling mixture of Cell Proliferation Kit II (XTT) are added to each well, and the plates are incubated at 37° C. After 1 to 3 hours, the absorbance at 490 nm (reference wavelength: 655 nm) is measured with a plate reader. Growth ratios of the cells in the wells treated with the test compounds are calculated based on the growth ratio of the cells in the control well treated with solvent (dimethyl sulfoxide (DMSO)) for 72 hours, which was defined as 100%. From a plot of test compound concentrations and the cell growth ratios at the concentrations, the concentration of 50% growth inhibition, the $GI_{50}$ value, are calculated.

Examples 27

Identification of Glycolipids Capable of Antiproliferative Activity in Hematologic Cancers WSU-NHL and Jurkat cells are seeded at 5,000 cells per well in 96-well plates in quadruplicates. Proliferation assays are performed for 96 hours. Tritiated thymidine (3H-TdR) incorporation during the last 16 hours of incubation was used to assess DNA synthesis. The responses of the compound of formula (1), (2), (3), (4), (5), (6), (7), (8), (9) or (10) to be tested is applied to the culture at a variety of concentrations at various time points beginning at 24, 18, 12, 6, and 0 hrs prior to antibody addition (anti-CD70).

Example 28

Protection of Cortical Cells from Apoptosis

To induce apoptosis, mouse cortical cells were cultured and treated with 50 µM hydrogen peroxide for three hours prior to being treated with the ganglioside analogue.

The cells were also treated with the hydrogen peroxide during treatment with the ganglioside analogue and post-treatment for 48 h. Cell death was assayed using the MTT assay.

Approximately 30% of the cells treated with hydrogen peroxide died as a result of the treatment. Treatment with GM1 (approx. 0.1 μM) provided approximately 20% protection of the cells from apoptosis.

Example 29

Protection of Cortical Cells from Cell Death

To induce non-apoptotic cell death, mouse cortical cells can be cultured and treated with 50 μM hydrogen peroxide and oligomycin (0.01 μM) for three hours prior to being treated with the ganglioside analogue. The cells are also treated with the hydrogen peroxide and oligomycin during treatment with the ganglioside analogue and post-treatment for 48 h. Cell death can be assayed using the MTT assay.

Approximately 30% of the cells treated with hydrogen peroxide can die as a result of the treatment. Treatment of the cells with compounds for use according to the invention protects approximately 20% protection of the cells from death.

Example 30

Animal Model of Parkinson's and atypical Parkinson's Disease

C57B1/6 mice 7-8 weeks of age can be treated with MPTP (b.i.d., 20 mg/kg, s.c.). The mice also receive a daily administration of saline, compound of formula (1), (2), (3), (4), (5), (6), (7), (8), (9) or (10) (1, 10 and 30 mg/kg, o.s.) or (0.3. to 3 mg/kg, i.p. or s.c.) for three weeks starting 24 h after the last MPTP injection. The brains are removed and analyzed for striatum and substantia nigra pars compacta dopamine levels. The midbrain is fixed for TH immunohistochemistry and dopamine neuron cell counts.

MPTP alone can cause approximately 76% loss of striatal dopamine. GM1a and compounds for use according to the invention increase striatal dopamine levels to approximately the same extent.

Examples 31

Animal Model of Huntington's Disease

Transgenic R6/2 mice, 40 day old, expressing human Huntingtin protein are administered compounds selected from (1) to (10) by intraperitoneal injection (3 or 30 mg/Kg) or oral gavage (30 mg/Kg), daily, for six weeks. Twice weekly, both control mice, receiving saline, and treated mice are assessed for disease progression using the rotorod test by methods known in the art.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the extent not inconsistent with the present disclosure.

What is claimed is:

1. A method of treating a subject having a GM3 deficiency, comprising administering to the subject a therapeutic amount of a compound selected from GM1 and GD1a.

2. The method of claim 1, wherein the subject has a GM3 synthase deficiency.

3. The method of claim 1, wherein the compound is GM1b.

4. The method of claim 1, wherein the subject is human.

5. The method of claim 1, wherein the compound is formulated for parenteral administration.

6. The method of claim 1, wherein the compound is GM1a.

7. The method of claim 1, wherein the compound is GD1a.

8. The method of claim 2, wherein the compound is GM1b.

9. The method of claim 2, wherein the compound is GM1a.

10. The method of claim 2, wherein the compound is GD1a.

* * * * *